United States Patent [19]

Dorsey et al.

[11] Patent Number: 5,502,053
[45] Date of Patent: Mar. 26, 1996

[54] HIV PROTEASE INHIBITOR COMPOUNDS

[75] Inventors: Bruce D. Dorsey, Harleysville; Joel R. Huff, Gwynedd Valley; Susan F. Britcher, Norristown, all of Pa.

[73] Assignee: Merck & Co., Inc., Rahway, N.J.

[21] Appl. No.: 294,772

[22] Filed: Aug. 23, 1994

Related U.S. Application Data

[63] Continuation of Ser. No. 944,568, Sep. 14, 1992, abandoned.

[51] Int. Cl.[6] ............... A61K 31/395; C07D 265/28
[52] U.S. Cl. .................... 514/239.2; 514/233.4; 514/432; 514/621; 544/162; 544/145; 549/23; 564/169; 564/164; 564/163; 564/158; 564/155
[58] Field of Search ............... 564/169, 155, 564/158, 163, 164; 514/621, 239.2, 233.5, 432; 544/162, 145; 549/23

[56] References Cited

U.S. PATENT DOCUMENTS

| | | | |
|---|---|---|---|
| 4,839,357 | 6/1989 | Patchett et al. | 514/235.8 |
| 5,132,400 | 7/1992 | Gammill et al. | 546/331 |
| 5,151,438 | 9/1992 | Sham et al. | 546/331 |

FOREIGN PATENT DOCUMENTS

| | | |
|---|---|---|
| 0229667 | 7/1987 | European Pat. Off. |
| 0337714 | 10/1989 | European Pat. Off. |
| 0356223 | 2/1990 | European Pat. Off. |
| 0357332 | 3/1990 | European Pat. Off. |
| 0364804 | 4/1990 | European Pat. Off. |
| 0434365 | 6/1991 | European Pat. Off. |
| 0480624 | 4/1992 | European Pat. Off. |
| 0480714 | 4/1992 | European Pat. Off. |
| 0482797 | 4/1992 | European Pat. Off. |
| 0487270 | 5/1992 | European Pat. Off. |

OTHER PUBLICATIONS

Power, M. D., et al., *Science*, 231, 1567–1572 (1986).
Kohl, N. E., et al., *Proc. Natl. Acad. Sci. USA: Biohemistry*, 85, 4686–4690, (1988).
Ratner, L., et al., *Nature*, 313, 277–284, (1985).
Toh, H., et al., *EMBO*, 4, 1267–1272, (1985).
Pearl, L. H., et al., *Nature*, 329, 351–354 (1987).
Beilstein on–line (computer printout—Ref. No. 1790871) (1993).
Denkwalter et al., Progress in Drug Research, vol. 10, pp. 510–512 (1966).
Burger, A. Medicinal Chemistry, 2nd Ed. pp. 565–571, 578–581, 600–601 (1960).
Haber et al., Renin Inhibitors: J. Cardiovascular Pharm. 10 Supp 7 A Search for Principles of Design, pp. 554–558 (1987).
Bolis et al. J. Med. Chem. 30, 1729–1737 (1987).
Plattner et al. J. Med. Chem., 31, 2277–2288 (1988).

*Primary Examiner*—Joseph K. McKane
*Attorney, Agent, or Firm*—Roy D. Meredith; Carol S. Quagliato; Melvin Winokur

[57] ABSTRACT

Compounds of formula

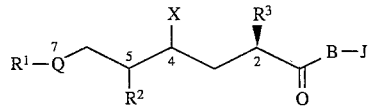

are HIV protease inhibitors, and are synthesized via a novel route. These compounds are useful in the prevention or treatment of infection by HIV and in the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

7 Claims, No Drawings

HIV PROTEASE INHIBITOR COMPOUNDS

This is a continuation of application Ser. No. 07/944,568, filed on Sep. 14, 1992, now abandoned.

The present invention is concerned with compounds which inhibit the protease encoded by human immunodeficiency virus (HIV) or pharmaceutically acceptable salts thereof, and a novel process for synthesizing them. These compounds are of value in the prevention of infection by HIV, the treatment of infection by HIV and the treatment of the resulting acquired immune deficiency syndrome (AIDS). It also relates to pharmaceutical compositions containing the compounds and to a method of use of the present compounds and other agents for the treatment of AIDS and vital infection by HIV.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a vitally encoded protease to generate mature vital proteins required for virus assembly and function. Inhibition of this processing prevents the production of normally infectious virus. For example, Kohl, N.E. et al., Proc. Nat'l Acad. Sci. 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., Nature, 313, 277(1985)]. Amino acid sequence homology provides evidence that the pol sequence encodes reverse transcriptase, an endonuclease and an HIV protease [Toh, H. et al., EMBO J. 4, 1267 (1985); Power, M.D. et al., Science, 231, 1567 (1986); Pearl, L. H. et al., Nature 329, 351 (1987)]. Applicants demonstrate that the novel compounds of this invention are inhibitors of HIV protease, and can be used for the treatment of infection by HIV and the treatment of the resulting AIDS disease. Applicants also describe an efficient, novel synthetic route for making the instant compounds.

BRIEF DESCRIPTION OF THE INVENTION

Compounds of formula I, as herein defined, and a process for making them are disclosed. These compounds are useful in the inhibition of HIV protease, the prevention of infection by HIV, the treatment of infection by HIV and in the treatment of AIDS, either as compounds, pharmaceutically acceptable salts, pharmaceutical composition ingredients, whether or not in combination with other antivirals, immunomodulators, antibiotics or vaccines. Methods of treating AIDS, methods of preventing infection by HIV, and methods of treating infection by HIV are also disclosed.

Some abbreviations that may appear in this application are as follows.

| ABBREVIATIONS | |
|---|---|
| Designation | Protecting Group |
| BOC (Boc) | t-butyloxycarbonyl |
| CBZ (Cbz) | benzyloxycarbonyl(carbobenzoxy) |
| TBS (TBDMS) | t-butyl-dimethylsilyl |
| | Activating Group |
| HOBt(HOBT or HBT) | 1-hydroxybenzotriazole hydrate |
| Designation | Coupling Reagent |
| BOP reagent | benzotriazol-1-yloxytris-(dimethylamino)phosphonium hexafluorophosphate |
| BOP-Cl | bis(2-oxo-3-oxazolidinyl) phosphinic chloride |
| EDC | 1-ethyl-3-(3-dimethylaminopropyl) carbodiimide hydrochloride |
| | Other |
| (BOC)$_2$O (BOC$_2$O) | di-t-butyl dicarbonate |
| n-Bu$_4$N$^+$F$^-$ | tetrabutyl ammonium fluoride |
| nBuLi (n-BuLi) | n-butyllithium |
| DMF | dimethylformamide |
| Et$_3$N | triethylamine |
| EtOAc | ethyl acetate |
| TFA | trifluoroacetic acid |
| DMAP | dimethylaminopyridine |
| DME | dimethoxyethane |
| LDA | lithium diisopropylamide |
| THF | tetrahydrofuran |
| Et$_2$O | diethyl ether |
| Bn | benzyl |
| DMSO | dimethyl sulfoxide |
| DIBAL-H (DIBAL) | diisobutylaluminum hydride |
| h | hour(s) |

DETAILED DESCRIPTION OF THE INVENTION AND PREFERRED EMBODIMENTS

This invention is concerned with compounds of formula I, combinations thereof, or pharmaceutically acceptable salts thereof, that are useful for the inhibition of HIV protease, the prevention or treatment of infection by HIV and in the treatment of the resulting acquired immune deficiency syndrome (AIDS). Compounds of formula I are defined as follows:

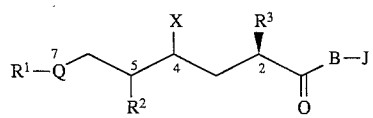

wherein

X is —OH, or —NH$_2$;

Q is

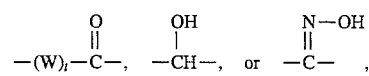

wherein W is —O— or —NR—, and t is zero or 1;

R is hydrogen or C$_{1-4}$ alkyl;

R$^1$ is 1) hydrogen,

—C$_{1-6}$ alkyl unsubstituted or substituted with one or more of a) hydroxy,
b) $C_{1-3}$ alkoxy,
c) —(W)$_t$-aryl, wherein W and t are defined above,
d) a 5–7 membered cycloalkyl group unsubstituted or substituted with one or more of
   i) hydroxy,
   ii) $C_{1-3}$ alkoxy, or
   iii) aryl,
e) heterocycle,
f) —NH—COOC$_{1-3}$alkyl,
g) —NH—Co—C$_{1-3}$alkyl,
h) —NH—SO$_2$C$_{1-3}$alkyl, or
i) —N(R)$_2$,
3) $C_{3-6}$ cycloalkyl group unsubstituted or substituted with one or more of
a) hydroxy,
b) $C_{1-3}$ alkoxy, or
c) aryl,
4) heterocycle, or
5) aryl, unsubstituted or substituted with one or more of $R^5$ as defined below, or $R^{15}$, wherein $R^{15}$ is:
a) hydroxy,
b) —NO$_2$ or —N(R)$_2$,
c) $C_{1-4}$alkyl,
d) $C_{1-3}$ alkoxy, unsubstituted or substituted with one or more of —OH, $C_{1-3}$ alkoxy, or aryl,
e) —CH$_2$N(R)$_2$,
f) —CH$_2$NHCOR,
g) —CF$_3$,
h) aryl,
i) —NHCOR,
j) —NRSO$_2$R, or
k) —OP(O)(OR$_x$)$_2$;

$R_x$ is H or aryl;

$R^2$ and $R^3$ are each independently —(CH$_2$)$_r$—R$^4$, wherein r is zero through 5;

$R^4$ is
1) hydrogen,
2) $C_{1-4}$ alkyl,
3) $C_5$–$C_{10}$ cycloalkyl, optionally substituted with hydroxy,
4) $C_6$–$C_{10}$ aryl, unsubstituted or substituted with one or more of $R^5$ or $R^{15}$,
5) monocyclic or bicyclic heterocycle containing from 1 to 3 heteroatoms chosen from the group consisting of N, O, and S and which is unsubstituted or substituted with $R^5$ and optionally with one or more of
a) halo,
b) $C_{1-4}$ alkyl, or
c) $C_{1-3}$ alkoxy;

$R^5$ is
1) —W$^1$—(CH$_2$)$_m$—NR$^6$R$^7$ wherein W$^1$ is —O—, —S—, or —NR—; m is 2–5; and R$^6$ and R$^7$ are each independently selected from:
a) hydrogen,
b) $C_{1-6}$ alkyl, unsubstituted or substituted with one or more of i) $C_{1-3}$ alkoxy, ii) —OH, or iii) —N(R)$_2$,
c) aromatic heterocycle unsubstituted or substituted with one or more of i) $C_{1-4}$ alkyl, or ii) —N(R)$_2$, or
d) $R^6$ and $R^7$ are joined together with the nitrogen to which they are attached to form a 5–7 member heterocycle, such as morpholino, containing up to two additional heteroatoms selected from —NR—, —O—, —S—, —SO—, or —SO$_2$—, the heterocycle optionally substituted with $C_{1-4}$ alkyl, 2) —(CH$_2$)$_q$—NR$^6$R$^7$ wherein q is 1–5, and R$^6$ and R$^7$ are defined above,
3) —O—((CH$_2$)$_m$O)$_p$—R, wherein m and R are defined above and p is 1–4, or
4) benzofuryl, indolyl, azacycloalkyl, azabicyclo $C_{7-11}$ cycloalkyl, or benzopiperidinyl, unsubstituted or substituted with $C_{1-4}$ alkyl;

B is absent, or $$-NH\underset{R^8}{\overset{\overset{Z}{\|}}{C}}-,$$

wherein
$R^8$ is
1) —CH(CH$_3$)$_2$,
2) —CH(CH$_3$)(CH$_2$CH$_3$),
3) —phenyl, or
4) benzyl;

J is:
1) —NHR$^9$, wherein R$^9$ is
a) hydrogen,
b) $C_{1-6}$ alkyl, unsubstituted or substituted with one or more of
   i) —N(R)$_2$,
   ii) —OR,
   iii) —NHSO$_2$C$_{1-4}$ alkyl,
   iv) —NHSO$_2$ aryl, or —NHSO$_2$(dialkylaminoaryl),
   v) —CH$_2$OR,
   vi) —C$_{1-4}$ alkyl,
   vii) —COOR,
   viii) —CON(R)$_2$,
   ix)

$$-\underset{NH}{\overset{}{NH}}\diagup N(R)_2 \quad \text{or} \quad -\underset{N-CN}{\overset{}{NH}}\diagup N(R)_2,$$

x) —NHCOR$^{13}$,
wherein
$R^{13}$ is
A) —H,
B) —heterocycle, or
C) —NHR$^{16}$, —OR$^{16}$ or —(CH$_2$)$_n$—R$^{16}$ wherein n is zero, 1, 2 or 3, and R$^{16}$ is
   I) —C$_{1-4}$ alkyl, unsubstituted or substituted with one or more of aryl or heterocycle, or
   II) aryl, unsubstituted or substituted with heterocycle,
   xi) —N(R)$_3^\oplus$ A$^\ominus$ wherein A$^\ominus$ is a counterion,
   xii) —NR$^{10}$R$^{11}$ wherein R$^{10}$ and R$^{11}$ are each independently C$_{1-5}$ alkyl and are joined together with the nitrogen to which they are attached to form a 5–7 membered heterocycle containing up to one additional heteroatom selected from —O—, —S—, or —NR—,
   xiii) aryl,
   xiv) —CHO,
   xv) —OP(O)(OR$_x$)$_2$, xvi)

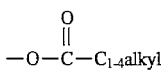

substituted with one or more of amine or quaternary amine, or —O—((CH$_2$)$_m$O)$_n$—R, or —OP(O)(OR$_x$)$_2$, xvii)

or xvii)

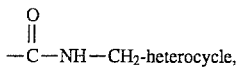

or
c) —((CH$_2$)$_m$O)$_n$CH$_3$ or —((CH$_2$)$_m$O)$_n$ H, wherein m and n are defined above,
2) —N(R$^9$)$_2$,
3) —NR$^{10}$R$^{11}$ wherein R$^{10}$ and R$^{11}$ are defined above, or
4)

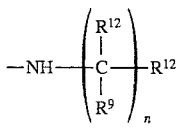

wherein R$^9$ and n are defined above; and
R$^{12}$ is
1) hydrogen,
2) aryl, unsubstituted or substituted with one or more of
  a) R$^{14}$, wherein R$^{14}$ is
    i) halo,
    ii) —OR,
    iii) —CON(R)$_2$,
    iv) —CH$_2$N(R)$_2$,
    v) —SO$_2$N(R)$_2$,
    vi) —N(R)$_2$,
    vii) —NHCOR,
    viii) C$_{1-4}$ alkyl,
    ix) phenyl
    x) —CF$_3$,
    xi) —NR—SO$_2$R,
    xii) —OP(O)(OR$_x$)$_2$, or
    xiii) —COOR,
    xiv) —C$_{1-4}$ alkyl-N(R)$_2$, or
  b)

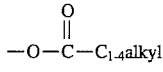

substituted with one or more of amine or quaternary amine or —OP(O)(OR$_x$)$_2$,
3) heterocycle, such as isochroman, chroman, isothiochroman, thiochroman, benzimidazole, benzothiopyran, oxobenzothiopyran, benzopyran, benzothiopyranylsulfone, benzothiopyranylsulfoxide, the ring or rings being unsubstituted or substituted with one or more of
  a) R$^{14}$, as defined above,
  b) —OC$_{1-4}$ alkenyl,
  c) —C$_{1-4}$ alkyl-phenyl,
  d)

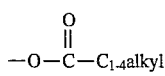

substituted with one or more of amine or quaternary amine, or —OP(O)(OR$_x$)$_2$, or —O((CH$_2$)$_m$O)$_n$—R, or
  e)

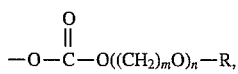

or
4) a 5 to 7 membered carbocyclic or 7–10 membered bicyclic carbocyclic ring, such as cyclopentane, cyclohexane, decalin, bicyclooctane, spirononane or indane, the carbocyclic ring being unsubstituted or substituted with one or more of
  a) R$^{14}$, as defined above,
  b) —CH$_2$OR,
  c) —(CH$_2$)$_n$—N(R)$_2$, C$_{5-16}$alkyl, pyridine, —(CH$_2$)$_n$NR—(CH$_2$)$_n$—N(R)$_2$, —(CH$_2$)$_n$—COOR, —((CH$_2$)$_m$O)$_n$—R, quinuclidiniumyl substituted with R, piperazine-C$_{1-4}$alkyl-benzyl substituted once or more with R, or morpholino-C$_{1-4}$alkyl-benzyl,
  d)

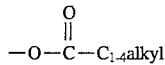

substituted with one or more of amine or quaternary amine, —OP(O)(OR$_x$)$_2$, or —O—((CH$_2$)$_m$O)$_n$—R,
  e)

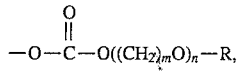

or
  f) —C$_{1-4}$alkyl-phenyl;
with the proviso that when Q is

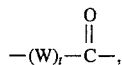

the compound of Formula I is not substituted with a primary or secondary amine;
or a pharmaceutically acceptable salt thereof.

A first preferred embodiment of this invention is limited to compounds of formula I having the following structural formula I-a

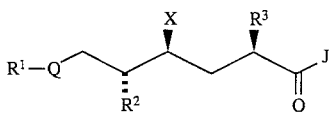

wherein
R$^1$ is
1) hydrogen,
2) —C$_{1-6}$ alkyl unsubstituted or substituted with one or more of
  a) hydroxy,
  b) C$_{1-3}$ alkoxy,
  c) —(W)$_t$-aryl, d) a 5–7 membered cycloalkyl group unsubstituted or substituted with one or more of
  i) hydroxy,
  ii) $C_{1-3}$ alkoxy, or
  iii) aryl,
e) heterocycle, or
f) —$N(R)_2$,
3) $C_{3-6}$ cycloalkyl group unsubstituted or substituted with one or more of
  a) hydroxy,
  b) $C_{1-3}$ alkoxy, or
  c) aryl, or
4) aryl, unsubstituted or substituted with one or more of $R^5$ as defined below, or $R^{15}$ wherein $R^{15}$ is:
  a) hydroxy,
  b) $C_{1-4}$ alkyl,
  c) $C_{1-3}$ alkoxy, unsubstituted or substituted with one or more of —OH, $C_{1-3}$ alkoxy, or aryl,
  d) —$CF_3$,
  e) —NHCOR, or
  f) —$NRSO_2R$;
$R^2$ and $R^3$ are each independently —$(CH_2)_r$—$R^4$, wherein r is 1 through 5;
$R^5$ is
  1) —O—$(CH_2)_m$—$NR^6R^7$,
  2) —$(CH_2)_q$—$NR^6R^7$, and $R^6$ and $R^7$ are each independently selected from:
    a) $C_{1-6}$ alkyl, unsubstituted or substituted with one or more of
      i) $C_{1-3}$ alkoxy,
      ii) —OH, or
      iii) —$N(R)_2$, or
    b) $R^6$ and $R^7$ are joined together with the nitrogen to which they are attached to form a 5–7 member heterocycle, such as morpholino, containing up to two additional heteroatoms selected from —NR—, —O—, —S—, —SO—, or —$SO_2$—, the heterocycle optionally substituted with $C_{1-4}$ alkyl, or
  3) —O—$((CH_2)_mO)_p$—R;
J is:
  1) —$NHR^9$, wherein $R^9$ is
    a) hydrogen,
    b) $C_{1-6}$ alkyl, unsubstituted or substituted with one or more of
      i) —$N(R)_2$,
      ii) —OR,
      iii) —$NHSO_2C_{1-4}$ alkyl,
      iv) —$NHSO_2$ aryl, or —$NHSO_2$(dialkylaminoaryl),
      v) —$CH_2OR$,
      vi) —$C_{1-4}$ alkyl,
      vii) —$CON(R)_2$,

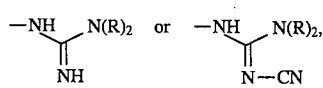

ix) —$NHCOR^{13}$,
      x) —$NR^{10}R^{11}$,
      xi) aryl,
      xii) —CHO
      xiii) —$OP(O)(OR_x)_2$, xiv)

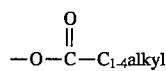

substituted with one or more of amine or quaternary amine, or —O—$((CH_2)_mO)_n$—R, or —$OP(O)(OR_x)_2$, xv)

or xvi)

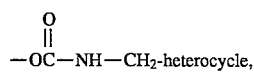

or

—$((CH_2)_mO)_nCH_3$ or —$((CH_2)_mO)_n$H, or
2)

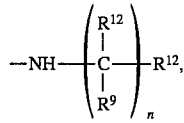

wherein $R^9$ and n are defined above; and
  $R^{12}$ is
    1) aryl, unsubstituted or substituted with one or more of
      a) $R^{14}$, wherein $R^{14}$ is
        i) halo,
        ii) —OR,
        iii) —$CON(R)_2$,
        iv) —$CH_2N(R)_2$,
        v) —$N(R)_2$,
        vi) —NHCOR,
        vii) —$C_{1-4}$ alkyl,
        viii) —$CF_3$, or
        ix) —NR—$SO_2R$,
        x) —$C_{1-4}$ alkyl-$N(R)_2$, or
      b)

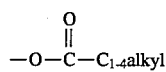

substituted with one or more of amine or quaternary amine or —$OP(O)(OR_x)_2$,
    2) heterocycle, such as isochroman, chroman, benzimidazole, benzothiopyran, benzopyran, benzothiopyranylsulfone, benzothiopyranylsulfoxide, the ring or rings being unsubstituted or substituted with one or more of
      a) $R^{14}$, as defined above,
      b) —$OC_{1-4}$ alkenyl, or
      c) —$C_{1-4}$ alkyl-phenyl, or a 5 to 7 membered carbocyclic or 7–10 membered bicyclic carbocyclic ring, the carbocyclic ring being unsubstituted or substituted with one or more of
      a) $R^{14}$, as defined above,
      b) —$CH_2OR$,
      c) —$(CH_2)_n$—$N(R)_2$, $C_{5-16}$alkyl, pyridine, —$(CH_2)_nNR$—$(CH_2)_n$—$N(R)_2$, —$(CH_2)_n$—COOR, —$((CH_2)_mO)_n$—R, quinuclidiniumyl substituted with R, piperazine- $C_{1-4}$alkylbenzyl substituted once or more with R, or morpholino-$C_{1-4}$alkyl-benzyl, d)

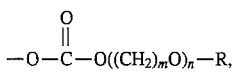

or
 e) —$C_{1-4}$alkyl-phenyl,
with all remaining variables as defined in formula I.

A second more preferred embodiment of this invention is further limited to compounds of formula I having structural formula I-a
wherein X is —OH,
 $R^1$ is
  1) hydrogen,
  2) —$C_{1-6}$ alkyl unsubstituted or substituted with one or more of
   a) hydroxy,
   b) $C_{1-3}$ alkoxy,
   c) —(W)$_t$-aryl,
   d) a 5-7 membered cycloalkyl group unsubstituted or substituted with one or more of
    i) hydroxy,
    ii) $C_{1-3}$ alkoxy, or
    iii) aryl, or
   e) heterocycle,
  3) —$C_{3-6}$ cycloalkyl group unsubstituted or substituted with one or more of
   a) hydroxy,
   b) $C_{1-3}$ alkoxy, or
   c) aryl, or
  4) aryl, unsubstituted or substituted with one or more of $R^{15}$, wherein $R^{15}$ is:
   a) hydroxy,
   b) $C_{1-3}$ alkoxy, unsubstituted or substituted with one or more of —OH, $C_{1-3}$ alkoxy or aryl,
   c) —NHCOR, or
   d) —NRSO$_2$R;
 $R^2$ and $R^3$ are each independently —(CH$_2$)$_r$—$R^4$, wherein r is 1 or 2;
 $R^4$ is
  1) $C_5$–$C_{10}$ cycloalkyl, optionally substituted with hydroxy, or
  2) $C_6$–$C_{10}$ aryl, unsubstituted or substituted with $R^5$, or with one or more of $R^{15}$ as defined above;
 $R^5$ is
  1) —O—(CH$_2$)$_2$—NR$^6$R$^7$, or
  2) —O—((CH$_2$)$_m$O)$_p$—R;
 J is

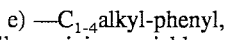

wherein n is zero, 1, 2, or 3, and
 $R^9$ is
  a) $C_{1-6}$ alkyl, unsubstituted or substituted with one or more of
   i) —N(R)$_2$,
   ii) —OR,
   iii) —NHSO$_2$C$_{1-4}$ alkyl,
   iv) —NHSO$_2$ aryl, or —NHSO$_2$(dialkylaminoaryl),
   v) —CH$_2$R,
   vi) —$C_{1-4}$ alkyl,
   vii) —CON(R)$_2$,
   viii) aryl, or
  ix)

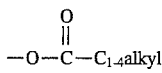

substituted with one or more of amine or quaternary amine, or —O—((CH$_2$)$_m$O)$_n$—R, or —OP(O)(OR$_x$)$_2$, or
  b) —((CH$_2$)$_m$O)$_n$CH$_3$ or —((CH$_2$)$_m$O)$_n$ H; and
 $R^{12}$ is
  1) aryl, unsubstituted or substituted with one or more of $R^{14}$, wherein $R^{14}$ is halo, —OR —NR—SO$_2$R, —$C_{1-4}$alkyl or —$C_{1-4}$alkyl-N(R)$_2$, or
  2) heterocycle, such as benzothiopyran, benzothiopyranylsulfone, benzothiopyranylsulfoxide, and enzimidazole, the ring or rings being unsubstituted or substituted with one or more of a) $R^{14}$ as defined above, or b) —$C_{1-4}$ alkyl-phenyl, or
  3) a 5-7 membered carbocyclic or 7-10 membered bicyclic carbocyclic ring, such as cyclopentane, cyclohexane, decalin, or indane, the carbocyclic ring being unsubstituted or substituted with one or more of
   a) $R^{14}$ as defined above,
   b) —CH$_2$OR, or
   c) —$C_{1-4}$alkyl-phenyl,
with all remaining variables as defined in formula I-a.

A third, most preferred embodiment of this invention is further limited to compounds of formula I having structural formula I-a wherein
 X is —OH,
 Q is

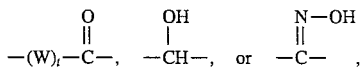

wherein
 W is —O— or —NH—, and t is zero or 1;
 $R^1$ is —$C_{1-6}$ alkyl unsubstituted or substituted with heterocycle or
 —$C_{5-7}$ cycloalkyl;
 $R^2$ is —CH$_2$—$C_{5-10}$cycloalkyl or —CH$_2$-phenyl,
 $R^3$ is —CH$_2$-phenyl, unsubstituted or substituted with one or more of 1) hydroxy,
  2) $C_{1-3}$ alkoxy unsubstituted or substituted with one or more of
   i) —OH,
   ii) $C_{1-3}$alkoxy, or
   iii) phenyl,
  3) —O(CH$_2$)$_2$-morpholinyl, or
  4) —O—((CH$_2$)$_m$O)$_p$—R wherein m is 2-5, p is 1-4 and R is hydrogen or $C_{1-4}$alkyl;
and J is

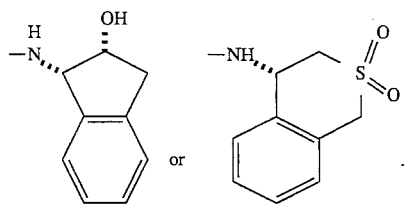

The most preferred compounds of this invention are compounds A through J, shown below, Compound A:

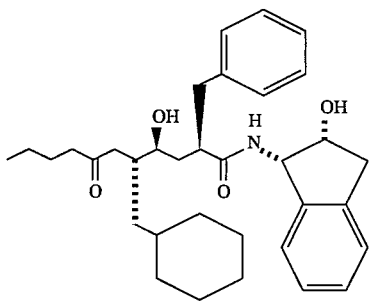

N-(2(R)-hydroxy-1(S)-indanyl)-5(R)-cyclohexylmethyl-4(S)-hydroxy-7-oxo-2(R)-phenylmethyl undecaneamide, Compound B:

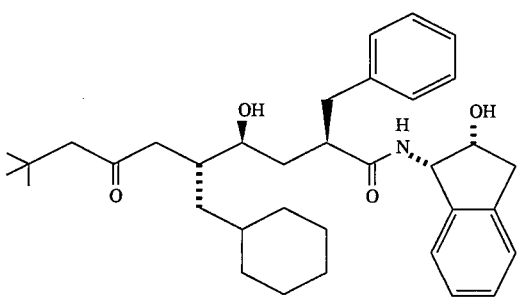

N-(2(R)-hydroxy-1(S)-indanyl)-5(R)-cyclohexylmethyl-9,9-dimethyl-4(S)-hydroxy-7-oxo-2(R)-phenylmethyl decaneamide, Compound C:

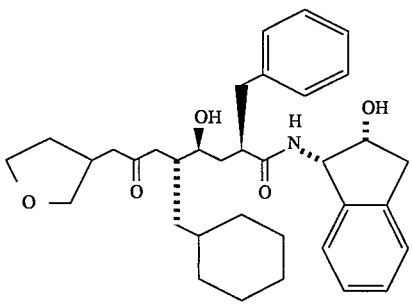

N-(2(R)-hydroxy-1(S)-indanyl)-5(R)-cyclohexylmethyl-4(S)-hydroxy-7-oxo-2(R)-phenylmethyl-8-(2'-tetrahydrofuran) octaneamide, Compound D:

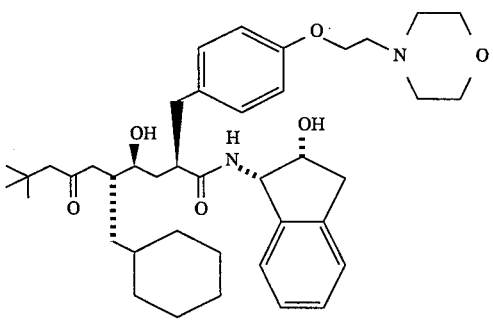

N-(2(R)-hydroxy-1(S)-indanyl)-5(R)-cyclohexylmethyl-9,9-dimethyl-4(S)-hydroxy-2(R)-((4-(2-(4-morpholinyl)ethoxy)phenyl) methyl)-7-oxo decaneamide, Compound E:

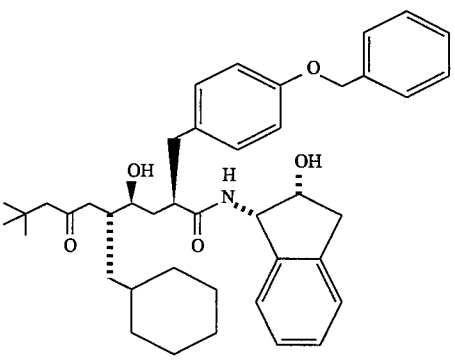

N-(2(R)-hydroxy-1(S)-indanyl)-5(R)-cyclohexylmethyl-9,9-dimethyl-4(S)-hydroxy-2(R)-((4-benzyloxyphenyl)methyl-7-oxo decaneamide, Compound F:

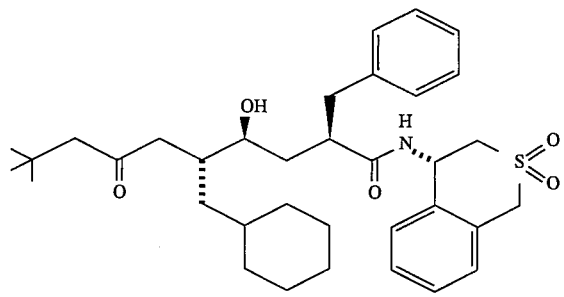

N-(4(S)-3,4-dihydro-1H-2,2-dioxobenzothiopyranyl)-5(R)-cyclohexylmethyl-9,9-dimethyl-4(S)-hydroxy-7-oxo-2(R)-phenylmethyl decaneamide, Compound G:

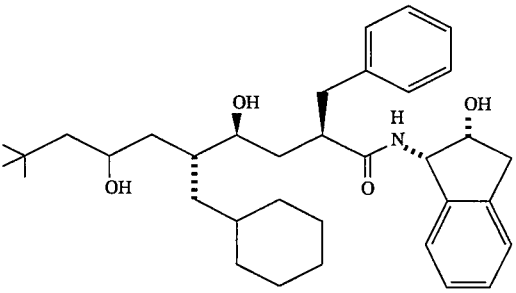

N-(2(R)-hydroxy-1(S)-indanyl)-5(R)-cyclohexylmethyl-9,9-dimethyl-4(S), 7-dihydroxy-2(R)-phenylmethyl decaneamide, Compound H:

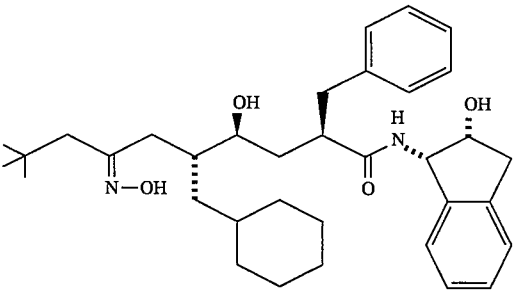

N-(2(R)-hydroxy-1(S)-indanyl)-5(R)-cyclohexylmethyl-9, 9-dimethyl-4(S)-hydroxy-7-oxime-2(R)-phenylmethyl decaneamide, Compound I:

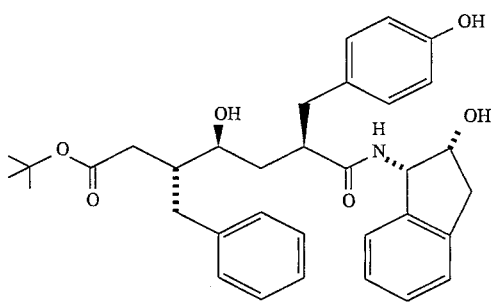

N-(2(R)-hydroxy-1(S)-indanyl)-6-(tert-butyloxycarbonyl)_4(S)-hydroxy-2(S)-(4-hydroxyphenyl)methyl-5(R)-phenylmethyl hexaneamide, Compound J:

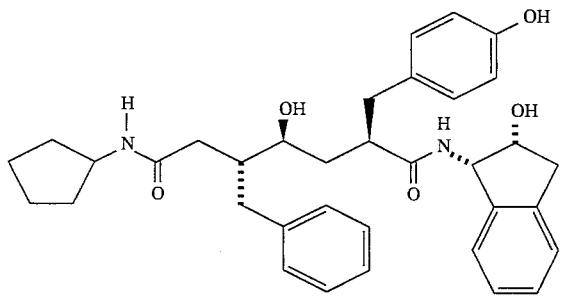

N-(2(R)-hydroxy-1(S)-indanyl)-N'-cyclopentyl-2(R)-(4-hydroxyphenyl)methyl-4(S)-hydroxy-5(R)-phenylmethyl heptane-1,7-dicarboxamide.

Novel compounds of the present invention also include but are not limited to the following compounds:

N-(2(R)-hydroxy-1(S)-indanyl)-5(R)-cyclohexylmethyl-4(S)-hydroxy-7-oxo-2(R)-phenylmethyl dodecaneamide, N-(2(R)-hydroxy-1(S)-indanyl)-5(R)-cyclohexylmethyl-4(S)-hydroxy-7-oxo-2(R)-phenylmethyl octaneamide, N-(2(R)-hydroxy-1(S)-indanyl)-5(R)-cyclohexylmethyl-8,8-dimethyl-4(S)-hydroxy-7-oxo-2(R)-phenylmethyl nonaneamide, N-(2(R)-hydroxy-1(S)-indanyl)-5(R)-cyclohexylmethyl-4(S)-hydroxy-7-oxo-7-phenyl-2(R)-phenylmethyl heptaneamide, N-(2(R)-hydroxy-1(S)-indanyl)-8-cyclohexyl-5(R)-cyclohexylmethyl-4(S)-hydroxy-7-oxo-2(R)-phenylmethyl octaneamide, N-(2(R)-hydroxy-1(S)-indanyl)-5(R)-cyclohexylmethyl-4(S)-hydroxy-7-oxo-8-phenyl-2(R)-phenylmethyl octaneamide, N-(4(S)-3,4-dihydro-1H-2,2-dioxobenzothiopyranyl)-5(R)-cyclohexylmethyl-4(S)-hydroxy-7-oxo-2(R)-phenylmethyl dodecaneamide, N-(4(S)-3,4-dihydro-1H-2,2-dioxobenzothiopyranyl)-5(R)-cyclohexylmethyl-4(S)-hydroxy-7-oxo-2(R)-phenylmethyl octaneamide, N-(4(S)-3,4-dihydro-1H-2,2-dioxobenzothiopyranyl)-5(R)-cyclohexylmethyl-8,8-dimethyl-4(S)-hydroxy-7-oxo-2(R)-phenylmethyl nonaneamide, N-(4(S)-3,4-dihydro-1H-2,2-dioxobenzothiopyranyl)-5(R)-cyclohexylmethyl-4(S)-hydroxy-7-oxo-7-phenyl-2(R)-phenylmethyl heptaneamide, N-(4(S)-3,4-dihydro-1H-2,2-dioxobenzothiopyranyl)-8-cyclohexyl-5(R)-cyclohexylmethyl-4(S)-hydroxy-7-oxo-2(R)-phenylmethyl octaneamide, N-(4(S)-3,4-dihydro-1H-2,2-dioxobenzothiopyranyl)-5(R)-cyclohexylmethyl-4(S)-hydroxy-7-oxo-8-phenyl-2(R)-phenylmethyl octaneamide, N-(2(R)-hydroxy-1(S)-indanyl)-5(R)-cyclohexylmethyl-4(S)-hydroxy-7-oxo-2(R)-phenylmethyl-8-(2')tetrahydrofuran octaneamide, N-(4(S)-3,4-dihydro-1H-2,2-dioxobenzothiopyranyl)-5(R)-cyclohexylmethyl-4(S)-hydroxy-7-oxo-2(R)-phenylmethyl-9-(2')-tetrahydrofuran octaneamide, N-(2(R)-hydroxy-1(S)-indanyl)-5(R)-cyclohexylmethyl-4(S)-hydroxy-2(R)-((4-(2-(4-morpholinyl)ethoxy)-phenyl)methyl)-7-oxo dodecaneamide, N-(2(R)-hydroxy-1(S)-indanyl)-5(R)-cyclohexylmethyl-4(S)-hydroxy-2(R)-((4-(2-(4-morpholinyl)ethoxy)-phenyl)methyl)-7-oxo octaneamide, N-(2(R)-hydroxy-1(S)-indanyl)-5(R)-cyclohexylmethyl-8,8-dimethyl-4(S)-hydroxy-2(R)-((4-(2-(4-morpholinyl)ethoxy)phenyl)methyl)- 7-oxo nonaneamide, N-(2(R)-hydroxy-1(S)-indanyl)-5(R)-cyclohexylmethyl-4(S)-hydroxy-2(R)-((4-(2-(4-morpholinyl)ethoxy)-phenyl)methyl)-7-oxo-7-phenyl heptaneamide, N-(2(R)-hydroxy-1(S)-indanyl)-5(R)-cyclohexylmethyl-4(S)-hydroxy-2(R)-((4-benzyloxyphenyl)methyl)-7oxo undecaneamide, N-(2(R)-hydroxy-1(S)-indanyl)-5(R)-cyclohexylmethyl-9,9-dimethyl-4(S)-hydroxy-2(R)-((4-benzyloxy-phenyl)methyl)-7-oxo decaneamide, N-(2(R)-hydroxy-1(S)-indanyl)-5(R)-cyclohexylmethyl-4(S)-hydroxy-2(R)-((4-benzyloxyphenyl)methyl)-7-oxo-9-(2')-tetrahydrofuran octaneamide, N-(2(R)-hydroxy-1(S)-indanyl)-5(R)-cyclohexylmethyl-4(S)-hydroxy-2(R)-((4-benzyloxyphenyl)methyl)-7-oxo dodecaneamide, N-(2(R)-hydroxy-1(S)-indanyl)-5(R)-cyclohexylmethyl-4(S)-hydroxy-2(R)-((4-benzyloxyphenyl)methyl)-7oxo octaneamide, N-(2(R)-hydroxy-1(S)-indanyl)-5(R)-cyclohexylmethyl-8,8-dimethyl-4(S)-hydroxy-2(R)-((4-benzyloxyphenyl)methyl)-7-oxo nonaneamide, N-(2(R)-hydroxy-1(S)-indanyl)-5(R)-cyclohexylmethyl-4(S)-hydroxy-2(R)-((4-benzyloxyphenyl)methyl)-7-oxo-7-phenyl heptaneamide, N-(2(R)-hydroxy-1(S)-indanyl)-8-cyclohexyl-5(R)-cyclohexylmethyl- 4(S)-hydroxy-2(R)-((4-benzyloxyphenyl)methyl)-7-oxo octaneamide, N-(2(R)-hydroxy-1(S)-indanyl)-5(R)-cyclohexylmethyl-4(S)-hydroxy-2(R)-((4-benzyloxyphenyl)methyl)-7-oxo-8-phenyl octaneamide, N-(2(R)-hydroxy-1(S)-indanyl)-5(R)-cyclohexylmethyl-4(S),7-dihydroxy-2(R)-phenylmethyl undecaneamide, N-(2(R)-hydroxy-1(S)-indanyl)-5(R)-cyclohexylmethyl-9,9-dimethyl-4(S),7-dihydroxy-2(R)-phenylmethyl decaneamide, N-(2(R)-hydroxy-1(S)-indanyl)-5(R)-cyclohexylmethyl-4(S),7-dihydroxy-2(R)-phenylmethyl-9-(2)tetrahydrofuran octaneamide, N-(2(R)-hydroxy-1(S)-indanyl)-5(R)-cyclohexylmethyl-4(S),7-dihydroxy-2(R)-phenylmethyl dodecaneamide, N-(2(R)-hydroxy-1(S)-indanyl)-5(R)-cyclohexylmethyl-4(S),7-dihydroxy-2(R)-phenylmethyl octaneamide, N-(2(R)-hydroxy-1(S)-indanyl)-5(R)-cyclohexylmethyl-8,8-dimethyl-4(S),7-dihydroxy-2(R)-phenylmethyl nonaneamide, N-(2(R)-hydroxy-1(S)-indanyl)-5(R)-cyclohexylmethyl-4(S),7-dihydroxy-7-phenyl-2(R)-phenylmethyl heptaneamide, N-(2(R)-hydroxy-1(S)-indanyl)-8-cyclohexyl-5(R)-cyclohexyl-methyl-4(S),7-dihydroxy-2(R)-phenylmethyl octaneamide, N-(2(R)-hydroxy-1(S)-indanyl)-5(R)-cyclohexylmethyl-4(S),7-dihydroxy-8-phenyl-2(R)-phenylmethyl octaneamide, N-(2(R)-hydroxy-1(S)-indanyl)-5(R)-cyclohexylmethyl-4(S),7-dihydroxy-2(R)-((4-(2-(4-morpholinyl)ethoxy)phenyl)methyl) octaneamide, N-(2(R)-hydroxy-1(S)-indanyl)-5(R)-cyclohexylmethyl-8,8-dimethyl-4(S),7-dihydroxy-2(R)-((4-(Z-(4-morpholinyl)ethoxy)phenyl)methyl) nonaneamide, N-(2(R)-hydroxy-1(S)-indanyl)-5(R)-cyclohexylmethyl-4(S),7-dihydroxy-2(R)-((4-(2-(4-morpholinyl)-ethoxy)phenyl)methyl)-7-phenyl heptaneamide, N-(2(R)-hydroxy-1(S)-indanyl)-5(R)-cyclohexylmethyl-4(S),7-dihydroxy-2(R)-((4-benzyloxyphenyl)methyl) undecaneamide, N-(2(R)-hydroxy-1(S)-indanyl)-5(R)-cyclohexylmethyl-9,9-dimethyl-4(S),7-dihydroxy-2(R)-((4benzyloxyphenyl)methyl) decaneamide, N-(2(R)-hydroxy-1(S)-indanyl)-5(R)-cyclohexylmethyl-4(S),7-dihydroxy-2(R)-((4-benzyloxyphenyl)-methyl)-9-(2')-tetrahydrofuran octaneamide, N-(2(R)-hydroxy-1(S)-indanyl)-5(R)-cyclohexylmethyl-4(S),7-dihydroxy-2(R)-((4-benzyloxyphenyl)methyl) dodecaneamide, N-(2(R)-hydroxy-1(S)-indanyl)-5(R)-cyclohexylmethyl-4(S),7-dihydroxy-2(R)-((4-benzyloxyphenyl)methyl) octaneamide, N-(2(R)-hydroxy-1(S)-indanyl)-5(R)-cyclohexylmethyl-4(S)-hydroxy-7-oxime-2(R)-phenylmethyl undecaneamide, N-(2(R)-hydroxy-1(S)-indanyl)-5(R)-cyclohexylmethyl-9,9-dimethyl-4(S)-hydroxy-7-oxime-2(R)-phenylmethyl decaneamide, N-(2(R)-hydroxy-1(S)-indanyl) -5(R)-cyclohexylmethyl-4(S)-hydroxy-7-oxime-2(R) -phenylmethyl-9-(2')tetrahydrofuran octaneamide, N-(2(R)-hydroxy-1(S)-indanyl) -5(R)-cyclohexylmethyl-9,9-dimethyl-7-oxime-2(R) -(4-(2-(4-morpholinyl)-ethoxy) phenyl)methyl)-4(S)-hydroxy decaneamide, N-(2(R)-hydroxy-1(S)-indanyl)-5(R)-cyclohexylmethyl-9,9-dimethyl-7-oxime-2(R) -((4-benzyloxyphenyl)-4(S)-hydroxy decaneamide, N-(2(R)-hydroxy-1(S)-indanyl)-6-(ethoxycarbonyl)-2(R)-(4-hydroxy)phenylmethyl-4(S)-hydroxy-5(R)-phenylmethyl hexaneamide, N-(2(R)-hydroxy-1(S)-indanyl)-N'-tert-butyl-2(R)-(4-benzyloxyphenyl)methyl- 4(S)-hydroxy-5(R)-phenylmethyl heptane-1,7-dicarboxamide, N-(2(R)-hydroxy-1(S)-indanyl)-6-(tert-butyloxycarbonyl)-2(R)-((4-benzyloxyphenyl)methyl)-4(S)-hydroxy-5(R)-phenylmethyl hexaneamide, N-(2(R)-hydroxy-1(S)-indanyl)-6-(tert-butyloxycarbonyl)-2(R)-((4-(2-(4-morpholinyl)ethoxy)phenyl) methyl)-4(S)-hydroxy-5(R)-phenylmethyl hexaneamide, N(2(R)-hydroxy-1(S)-indanyl)-6-(isopropyloxycarbonyl)-4(S)-hydroxy-2(R)-phenylmethyl-5(R)-phenylmethyl hexaneamide, N-(2(R)-hydroxy-1(S)-indanyl)-N'-tert-butyl-4(S)-hydroxy-2(R)-phenylmethyl-5(R)-phenylmethyl heptane-1,7-dicarboxamide, N-(2(R)-hydroxy-1(S)-indanyl)-N'-tertbutyl-2(R)-((4-(2-(4-morpholinyl)ethoxy)phenyl)methyl)-4(S)-hydroxy-5(R)-phenylmethyl heptane-1,7-dicarboxamide.

The compounds of the present invention, may have asymmetric centers and occur as racemates, racemic mixtures and as individual diastereomers, with all isomeric forms being included in the present invention.

When any variable (e.g., aryl, heterocycle, R, $R^1$, $R^2$, $A^\ominus$, n, Z, etc.) occurs more than one time in any constituent or in structural formula, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge; and "cycloalkyl" is intended to include saturated ring groups, such as cyclopropyl, cyclobutyl, cyclopentyl, cyclohexyl (Cyh) and cycloheptyl. "Alkenyl" is intended to include hydrocarbon groups of either a straight or branched configuration with one or more carbon-carbon double bonds which may occur in any stable point along the chain, such as ethenyl, propenyl, butenyl, pentenyl, and the like. "Alkynyl" is intended to include hydrocarbon groups of either a straight or branched configuration with one or more carbon-carbon triple bonds which may occur in any stable point along the chain, such as ethynyl, propynyl, butynyl, pentynyl, and the like. "Halo", as used herein, means fluoro chloro, bromo and iodo; and "counterion" is used to represent a small, single negatively-charged species, such as chloride, bromide, hydroxide, acetate, trifluroacetate, perchlorate, nitrate, benzoate, maleate, tartrate, hemitartrate, benzene sulfonate, and the like.

As used herein, with exceptions as noted, "aryl" is intended to mean phenyl (Ph) or naphthyl. "Carbocyclic" is intended to mean any stable 5- to 7-membered carbon ring or 7- to 10-membered bicyclic carbon ring any ring of which may be saturated or unsaturated such as cyclopentane, cyclohexane, decalin, bicyclooctane, spirononane, and indane. Preferred carbocyclic rings are cyclopentane, cyclohexane, decalin and indane.

The term heterocycle or heterocyclic, as used herein except where noted, represents a stable 5- to 7-membered mono- or bicyclic or stable 7- to 10-membered bicyclic heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl. Preferred heterocycles in this invention are piperazinyl, pyrrolyl, imidazolyl, morpholinyl, quinolinyl, isoquinolinyl, benzimidazolyl, benzopyranyl, benzothiopyranyl, benzothiopyranylsulfone, tetrahydrofuryl, and tetrahydropyranyl.

The pharmaceutically-acceptable salts of the compounds of Formula I (in the form of water- or oil-soluble or dispersible products) include the conventional non-toxic salts or the quaternary ammonium salts which a re formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, rosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Amide couplings used to form the compounds of this invention are typically performed by the carbodiimide method with reagents such as dicyclohexylcarbodiimide (DCC), or 1-ethyl-3-(3-dimethylamino-propyl) carbodiimide (EDC). An amide coupling reagent such as BOP may also be used. Other methods of forming the amide or peptide bond include, but are not limited to the synthetic routes via an acid chloride, azide, mixed anhydride or activated ester. Typically, solution phase amide coupling are performed, but solid-phase synthesis by classical Merrifield techniques may be employed instead. The addition and removal of one or more protecting groups is also typical practice. Additional related information on synthetic background is contained in EPO 0337714.

Preferred methods for preparing the novel compounds of this invention are presented below. Variables used in the method descriptions (e.g. $R^1$, $R^2$, B, etc.) correspond to those defined in the generic description of formula I, except where otherwise noted. Tables 1–5 which follow the methods illustrate the compounds that can be synthesized by the described methods, but the described methods are not limited by the compounds in the tables nor by any particular substituents that may be employed in the method descriptions for illustrative purposes. The examples specifically illustrate the application of the following methods to specific compounds.

Compounds of formula II are most preferably prepared by condensation of about 1–3 equivalents of an unsaturated aldehyde of formula 1

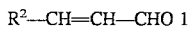

with about 1 equivalent of an acylated oxazolidinone of formula 2

under an inert atmosphere at a low temperature, e.g. between about −100° C. and ambient temperature or preferably between about −78° C. and 0° C., in an etherial solvent or $CH_2Cl_2$, with $CH_2Cl_2$ being preferred, to produce 3

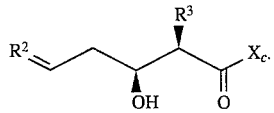

This condensation reaction is done in the presence of about 1 equivalent of an amine base such as diisopropyl ethylamine and about 1 equivalent of dialkylboron trilate. Etherial solvents include THF, DME, $Et_2O$, and methyl-t-butyl ether. Conditions for aldol reactions are known in the art and are described in e.g., Evans, D. A., et al., *J. Am. Chem. Soc.*, 103, 2127–2129 (1981).

In formula 2, $X_c$ represents a chiral auxiliary group which serves to direct formation of the desired diastereomer of the adduct 3 in high yield. The $X_c$ group is preferably 4(R)-phenylmethyl-2-oxazolidinonyl ($X_{c-1}$ below), or 4(R)-methyl-5(S)-phenyl-2-oxazolidinonyl ($X_{c-2}$ below), with 4(R)-phenylmethyl-2-oxazolidinonyl being most preferred.

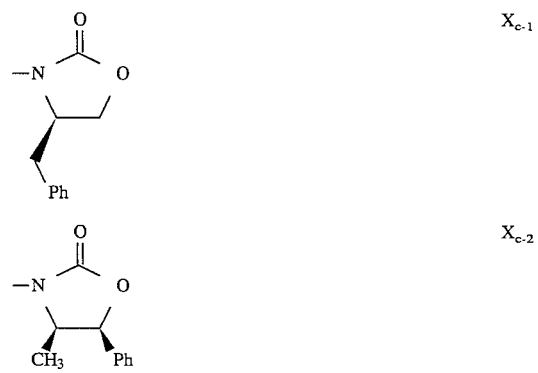

Upon treatment of about 1 equivalent of Compound 3 with about 10 equivalents of trimethyl orthoacetate or triethyl orthoacetate, with triethyl orthoacetate being preferred, in the presence of a catalytic amount of a weak carbon acid such as isobutyric acid, compound 3 undergoes a Claisen rearrangement to produce 4

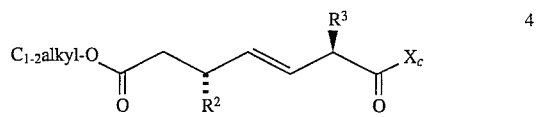

followed by hydrolysis with base to form the acid 5

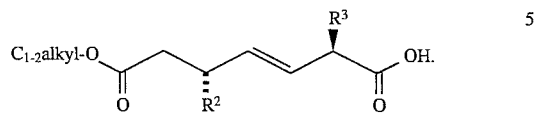

The Claisen reaction is done at a temperature between about room temperature to 140° C., preferably between about 100° C. to 120° C., using a drying tube filled with, e.g. $CaSO_4$. The reaction can be done using toluene, xylene or diglyme as solvent. Reaction conditions for the Claisen rearrangement are well known in the art and are described, e.g., in the following publications: Ireland, R. E., et al, *J. Am. Chem. Soc.*, 94, 5897–5898 (1972); Johnson, W. S., et al., *J. Am. Chem. Soc.*, 92, 741–743 (1970); and Felix, D., et al., *Helv. Chim. Acta*, 52, 1030–1042 (1969).

Any base suitable for the hydrolysis of 4 to 5 may be used, and examples include aqueous NaOH, LiOH, KOH, or lithium hydrogen peroxide, with lithium hydrogen peroxide being preferred. About 1.5 equivalents of lithium hydrogen peroxide is sufficient for hydrolyzing 1 equivalent of compound 4, and the hydrolysis can be carried out at a temperature between about −20° C. to room temperature, with about 0° C. being preferred, in water or an etherial solvent or a mixture thereof.

The acid 5 is coupled to an amine of formula H-B-J in an etherial solvent, DMF or CH$_2$Cl$_2$, with DMF or CH$_2$Cl$_2$ being preferred, using standard peptide coupling techniques to form the amide 6

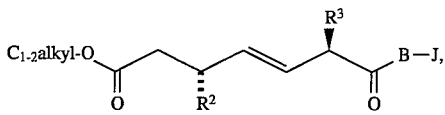

wherein B may be absent, as defined above. About 1.2 equivalents of H-B-J amine is coupled to 1 equivalent of acid 5. The coupling is preferably done under an inert atmosphere, although an inert atmosphere is not required, at a temperature in the range of about −20° C. to 40° C. Preferably, the reaction is started at about 0° C., then left to warm to ambient temperature on its own. Preferably, the amide coupling is accomplished using about 1.2 equivalents each of HOBt and EDC in the presence of about 1.2 equivalents of base such as triethylamine, although other coupling conditions well known to those skilled in the art may be used.

Next, the ester 6 is hydrolyzed with about 10 equivalents of a base, such as LiOH, NaOH, or KOH, with LiOH in DME/H$_2$O being preferred, at a temperature in the range of −20° C. to 40° C., with about 0° C. to ambient being the preferred range, to afford 7

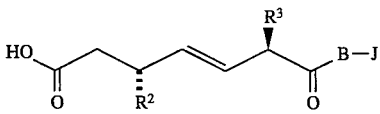

followed by halo-lactonization to form 8

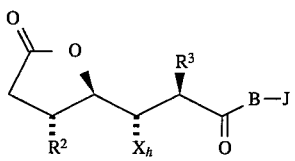

wherein X$_h$ is —I or —Br, with —I being preferred. Lactone 8 is next reduced to 9

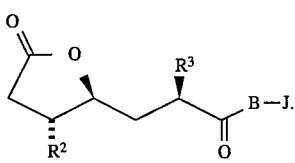

There are many possible halogen sources and appropriate solvents known to those skilled in the art that can be used in the lactonization step, and examples include I$_2$, NaHCO$_3$, 4,4'-thiobis(2-tertbutyl- 6-methylphenol), in CH$_2$Cl$_2$/H$_2$O; I$_2$, CH$_3$CN; KI$_3$, Et$_2$O, NaHCO$_3$; N-bromosuccinimide (NBS), DMF; or N-iodosuccinimide (NIS), THF, 4,4'-thiobis(2-tertbutyl-6-methylphenol); with the most preferred being the reaction done in the dark using NIS, THF, 4,4'-thiobis(2-tert-butyl-6-methylphenol). A catalytic amount of 4,4'-thiobis(2-tert-butyl-6-methylphenol) is used to inhibit free radical formation. About 10 equivalents of NIS is used per equivalent of acid 7. The lactonization step can be run in a temperature range of about −20° C. to ambient, and is preferably run at ambient temperature. An inert atmosphere is preferred. This reaction step is done in a suitable solvent such as an etherial solvent or CH$_2$Cl$_2$, with an etherial solvent such as THF being preferred.

Compound 8 is preferably reduced with a catalytic amount of azobisisobutyro-nitrile (AIBN) and about 1.2 equivalents of a trialkyltin hydride per equivalent of Compound 8. The reduction can be run at an elevated temperature between about 120° C. to ambient, with about 80° C. being preferred, in, e.g., refluxing benzene, toluene, or an etherial solvent, with benzene or toluene preferred. Tributyltin hydride is the preferred source of hydride. An inert atmosphere is preferred, though not required.

Finally, about one equivalent of lactone 9 is reacted with about 3.2 equivalents of a lithium reagent of formula R$^1$-Li at low temperature in an etherial solvent under an inert atmosphere to produce the compounds of formula II in equilibrium with lactol 10.

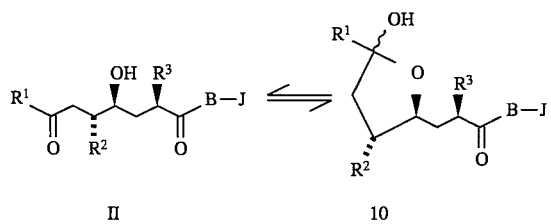

The reaction should be run at a low temperature, e.g., preferably in the range of about −100° C. to 0° C., more preferably in the range of about −78° C. to 0° C., and most preferably in the range of about −78° C. to −20° C. The etherial solvents that may be used are any solvents suitable for use in this reaction step, including, e.g., THF, DME, Et$_2$O, and methyl-t-butyl ether, with THF or Et$_2$O being preferred. Compounds of Formula II are recovered and purified by standard techniques known in the art, e.g. silica gel chromatography.

When J is N-2(R)-hydroxy-1(S)-indanyl, it is preferable to protect the indanyl group of compound 7 as the acetonide (see Example 1, step 7) before the halo-lactonization step in order to obtain the desired stereoisomer of lactone 8. Protection of the indanyl group is accomplished by treating one equivalent of the acid-indane 7 with about 2 equivalents of 2-methoxy propene and a catalytic amount of p-toluensulfonic acid pyridine salt (pPTS). An inert atmosphere is preferred, but not required, and the protection can be done in a temperature range of about −78° C. to 40° C., with ambient temperature preferred. The reaction can be done in an etherial solvent or CH$_2$Cl$_2$, with CH$_2$Cl$_2$ preferred. Lactonization can be accomplished absent protection of the indanyl group, but it results in a mixture of lactone stereoisomers. The protecting group is removed at the end of the synthetic sequence (see Example 1, step 11). (1S, 2R)-Cis-1-amino-2-indanol is prepared from commercially available indene according to standard techniques well known in the art to one of ordinary skill such as, for example, the procedures disclosed in Hassner, et al., *J. Org. Chem,*, 32, 540 (1967), and resolved according to standard techniques well known in the art.

The aldehyde of formula 1 can be prepared as shown in Scheme I, below.

Scheme I

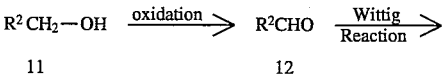

Scheme I
-continued

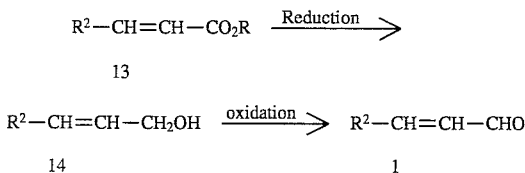

The alcohol 11 can be converted to the ester by employing a Swern oxidation followed by a Wittig reaction, as described in Ireland, R. E., et al., *J. Org. Chem.*, 50, 2198–2200 (1985). The ester is then reduced to the alcohol 14, then oxidized to the aldehyde 1 using techniques well-known to those skilled in the art.

The chiral auxiliary is incorporated into compound 2 by standard amide coupling methods well known in the art, such as, e.g., forming the mixed anhydride of $R^3$—$CH_2$—COOH with trimethylacetyl chloride and $Et_3N$, then treating it with the lithium salt of either commercially available 4(R)-phenylmethyl-2-oxazolidinone or 4(R)-methyl-5(S)-phenyl-2-oxazolidinone to form compound 2.

Compounds of Formula I where X is —$NH_2$ can be made by converting the acid group of 7 to a primary amide then forming an imino ester by treating the amide with e.g., trimethylsilyl triflate/$Et_3N$ (e.g., see Knapp, S., *Tetrahedron Letters*, 26, 1803–1806 (1985)) before treating the compound with a halogen as described, so as to form the halo-lactam analog of compound 8. After reduction to remove the halo group, the lactam nitrogen is protected with, e.g., a —BOC group, and then the protecting group is removed by treatment with acid after completion of the remaining synthetic steps.

By reducing a compound of formula I where Q is —CO— using methods well known in the art (e.g., with $NaBH_4$), compounds of formula I where Q is —CHOH— can be made. By reacting a compound of formula I where Q is —CO— with hydroxylamine . HCl and base, such as $K_2CO_3$, compounds of formula I where Q is —C=NOH— can be made.

Another method for synthesizing the compounds of this invention is exemplified below in Scheme II. In Step A, the carboethoxy group of 3-carboethoxy-5-((1-benzyloxymethoxy)-2-phenylethyl-dihydrofuran-2(3H)-one (compound 15-preparation described in Example 12) can be replaced by an alkylation, ring-opening, decarboxylation, re-lactonization sequence as follows: treatment of 15 with an aprotic base such as sodium hydride, addition of benzyloxy benzylchloride at 25°–50° C., then hydrolytic opening of the lactone ester with a base such as sodium or lithium hydroxide, followed by treatment with acid, then decarboxylation/relactonization at an elevated temperature such as in refluxing toluene. The diastereomeric product can be recovered, and the diastereomers separated by standard techniques well-known to those skilled in the art. In Step B, the benzyloxymethoxy protecting group can be removed by standard methods known in the art, such as with Na or Li in ammonia, or preferably by treatment with thiophenol and boron trifluoride etherate in an appropriate solvent, e.g., anhydrous $CH_2Cl_2$, at about 25° C. to obtain 17. In Step C, the deprotected alcohol 17 is converted to a ketone using an appropriate oxidizing agent, for instance under Swern conditions or, preferably, with Dess-Martin periodinane, under dry conditions in an appropriate solvent, such as $CH_2Cl_2$, to obtain 18. In Step D, a Wittig reaction is employed to obtain 19. For example, 18 is reacted with t-butoxycarbonylmethylene triphenylphosphorane under dry conditions in an appropriate solvent, such as benzene, to obtain 19. In Step E, the lactone ring is hydrolyzed open with a base, such as LiOH, and the resulting 4-position alcohol of 20 is protected with one of the silyl ether protecting groups known in the art, such as a t-butyl dimethylsilyl (TBDMS) protecting group. Employing standard amide coupling techniques well known in the art in Step F, such as the carbodiimide method, using e.g., HOBt with dimethyl-3-(3-dimethylaminopropyl) carbodiimide hydrochloride, amino indanol is coupled to 20, the resulting diastereomers are separated, and the TBDMS hydroxy protecting group is removed by treatment with fluoride e.g., tetrabutylammonium fluoride to obtain 21. The final product, 22, is obtained in Step G by reducing the olefinic product 21 using standard catalytic hydrogenation techniques known in the art, e.g., hydrogenation at room temperature in the presence of a catalyst such as palladium hydroxide on carbon, in an appropriate solvent, e.g., ethanol.

Scheme II

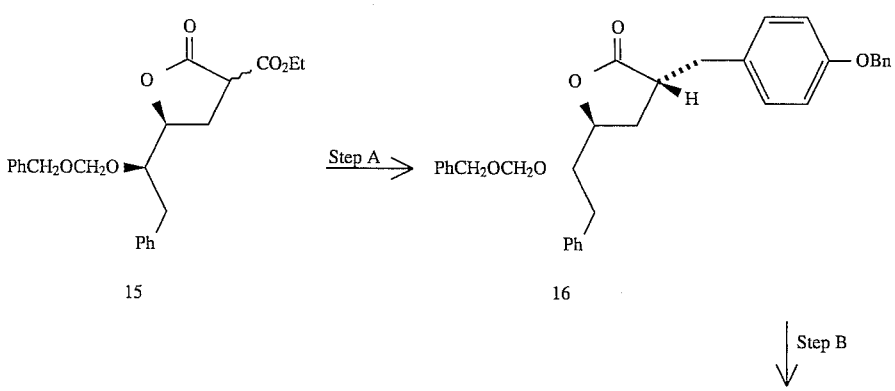

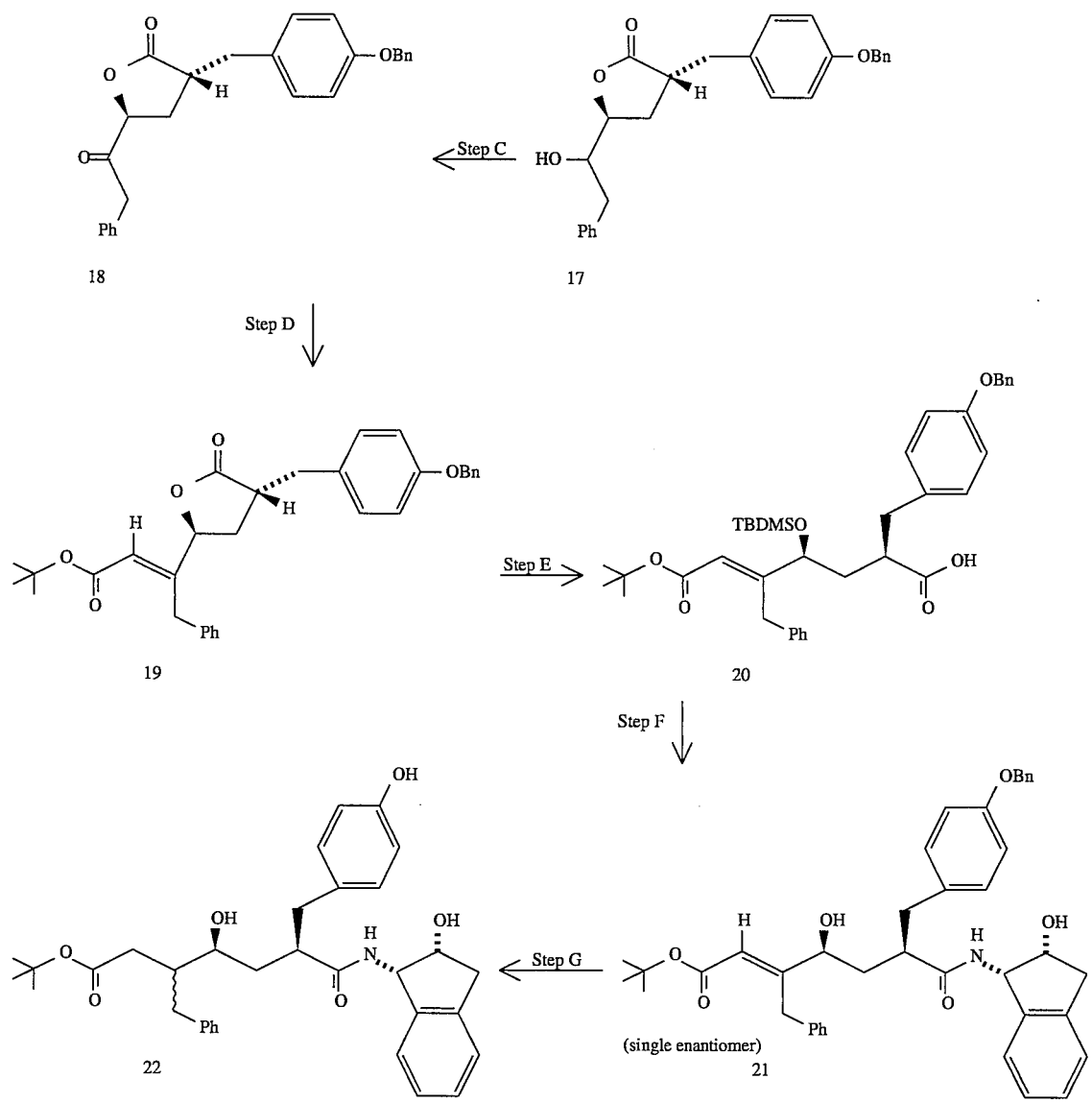

A compound of formula I wherein $R^1$—Q— is $NRR^1$—CO— can be made by first removing the t-butyl group from compound 19 (above in Scheme II) with an acid in an appropriate solvent, such as trifluoracetic acid in $CH_2Cl_2$, then coupling an amine of formula $NHRR^1$ to the carboxylic acid derivative of 19, and then proceeding with remaining Steps E through G as described for Scheme II.

The compounds of this invention are also illustrated by the following tables.

TABLE 1
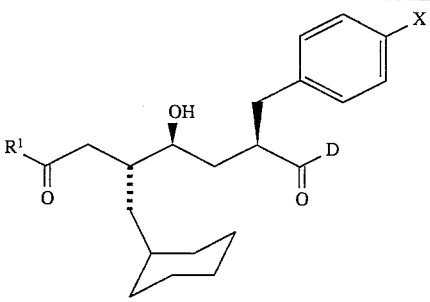
| R₁ | X | D |
|---|---|---|
| (CH₃)₃C-CH₂- | OH | 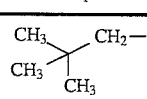 |
| (CH₃)₃C-CH₂- | OH | 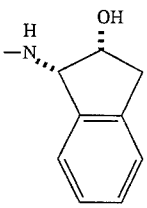 |
| (CH₃)₃C-CH₂- | OH | 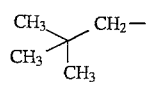 |
| (CH₃)₃C-CH₂- | OH | 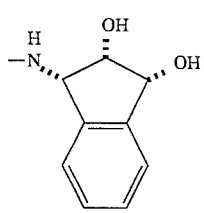 |
| (CH₃)₃C-CH₂- | OH | 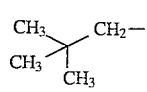 |
| (CH₃)₃C-CH₂- | OH | 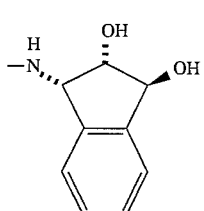 |
| (CH₃)₃C-CH₂- | OH | 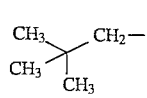 |

TABLE 1-continued

| R₁ | X | D |
|---|---|---|
| (CH₃)₃C-CH₂- | H | -NH-(2-hydroxy-indan-1-yl) |
| (CH₃)₃C-CH₂- | H | -NH-(1,2-dihydroxy-indan-3-yl) |
| (CH₃)₃C-CH₂- | H | -NH-(2-methyl-cyclopentan-1-ol-3-yl) |
| (CH₃)₃C-CH₂- | H | -NH-CH(CH₂-benzo-sulfone) |
| (CH₃)₃C-CH₂- | H | -NH-CH(iPr)-C(O)-NH-CH₂-(1H-benzimidazol-2-yl) |
| (CH₃)₃C-CH₂- | -O-CH₂-C₆H₅ | -NH-(2-hydroxy-indan-1-yl) |

TABLE 1-continued

TABLE 1-continued
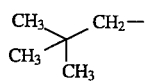
| R₁ | X | D |
|---|---|---|
| 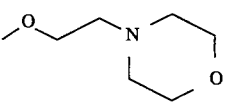 | 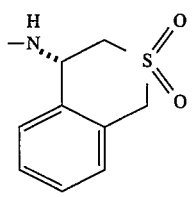 | 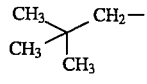 |
| 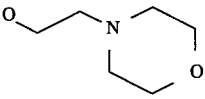 | 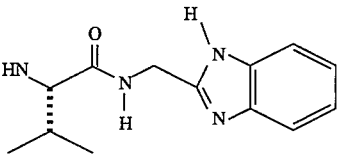 | 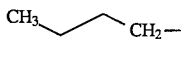 |
| 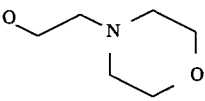 | 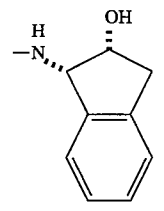 |  |
| 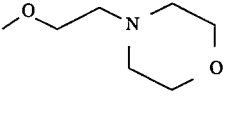 | 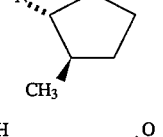 |  |
| 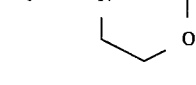 | 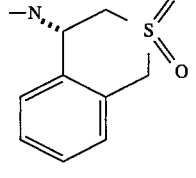 | 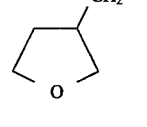 |
| 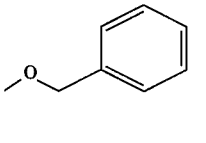 | 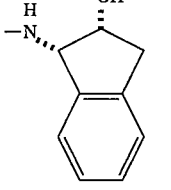 | 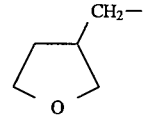 |
| 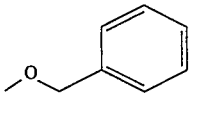 | 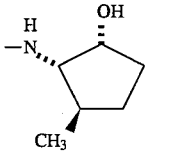 | |

TABLE 1-continued
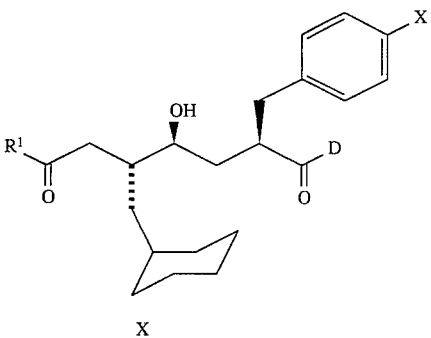
| R₁ | X | D |
|---|---|---|
| 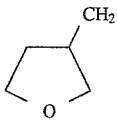 | 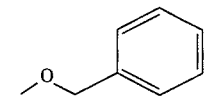 | 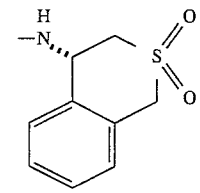 |
| 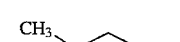 | 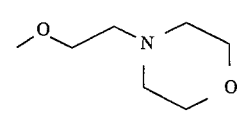 | 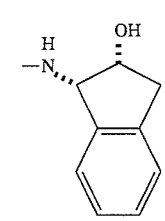 |
|  | 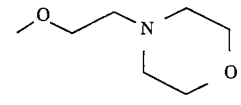 | 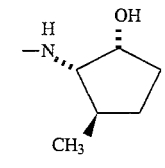 |
| 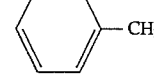 | 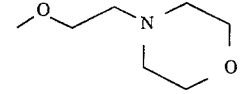 | 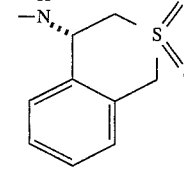 |
| 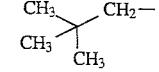 | 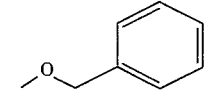 | 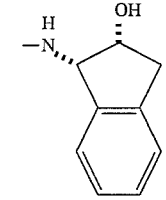 |
| 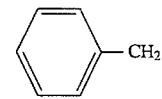 | 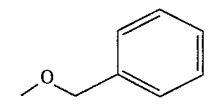 | 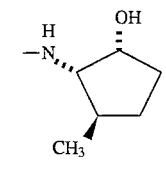 |

TABLE 1-continued
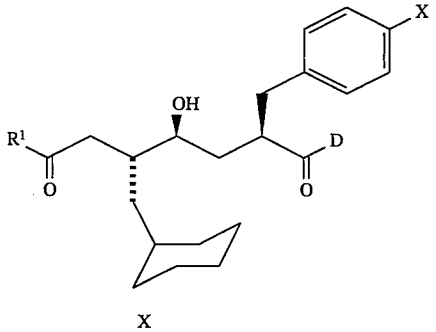

TABLE 1-continued

[Structure: chain with R¹−C(=O)−CH₂−CH(CH₂-cyclohexyl)−CH(OH)−CH₂−CH(CH₂-C₆H₄-X)−C(=O)−D]

| R₁ | X | D |
|---|---|---|
| HO−C₆H₄−CH₂− | OH | −NH−CH(CH₂SO₂CH₂-o-phenylene)− (isothiochroman-2,2-dioxide substituent) |

TABLE 2

[Structure: HO−CH(R¹)−CH₂−CH(CH₂-cyclohexyl)−CH(OH)−CH₂−CH(CH₂-C₆H₄-X)−C(=O)−D]

| R¹ | X | D |
|---|---|---|
| C₆H₅− | H | −NH−(1-indanyl with 2-OH) |
| C₆H₅−CH₂− | H | −NH−(2-hydroxy-3-methylcyclopentyl) |
| CH₃−O−CH₂− | H | −NH−CH(CH₂SO₂CH₂-o-phenylene)− (isothiochroman-2,2-dioxide substituent) |

TABLE 2-continued
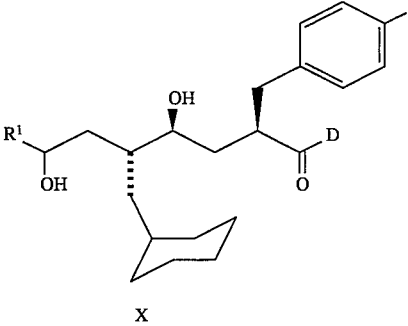
| R¹ | X | D |
|---|---|---|
|  | 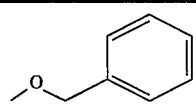 | 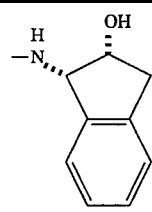 |
| 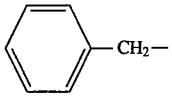 | 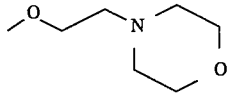 | 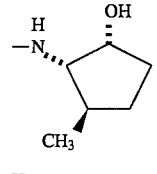 |
| 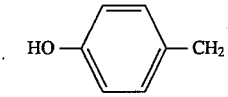 | OH |  |
| 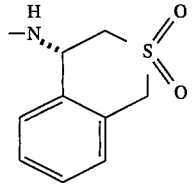 | H | 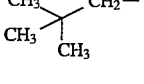 |
| 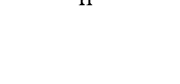 | 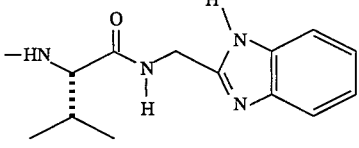 | 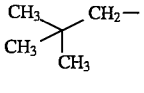 |
| 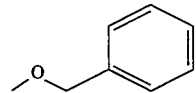 | 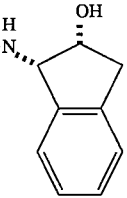 | 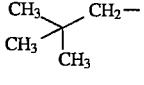 |
| 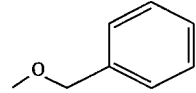 | 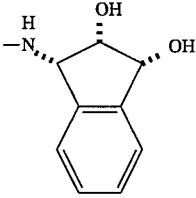 | 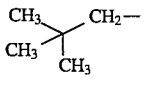 |

TABLE 2-continued
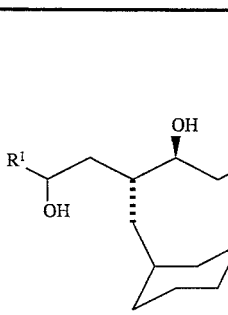
| R¹ | X | D |
|---|---|---|
| 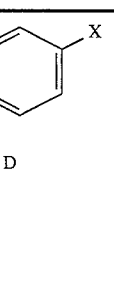 |  | 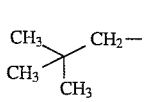 |
| 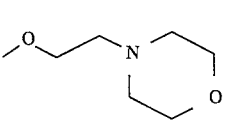 | 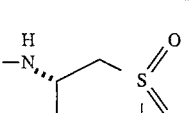 | 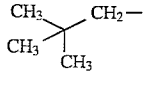 |
TABLE 3
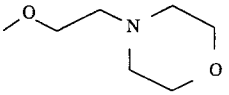
| R¹ | X | D |
|---|---|---|
| 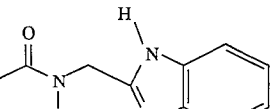 | H | 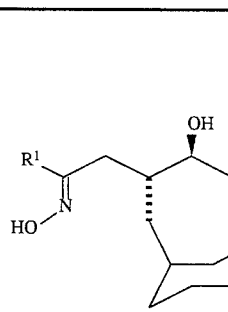 |
| 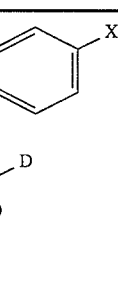 | H |  |

TABLE 3-continued
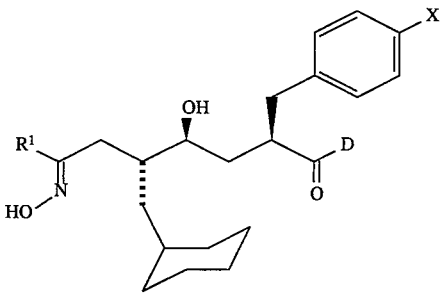
| R¹ | X | D |
|---|---|---|
| 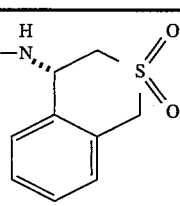 | H | 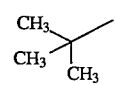 |
| 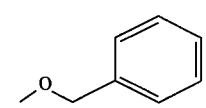 | 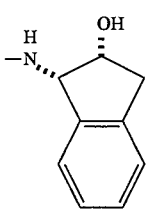 | 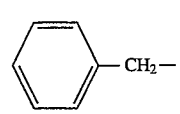 |
| 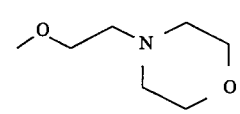 | 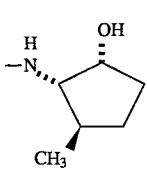 | 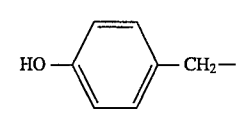 |
| 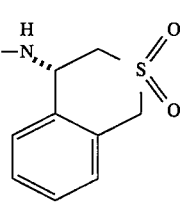 | OH | 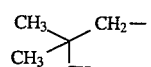 |
| 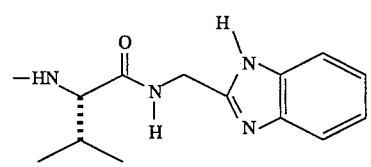 | H | 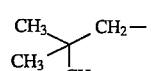 |
| 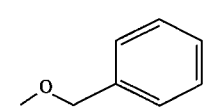 | 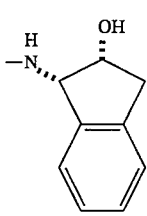 | |

TABLE 3-continued
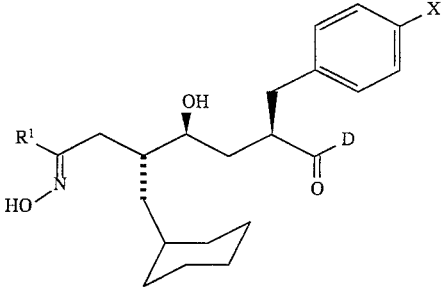
| R¹ | X | D |
|---|---|---|
| 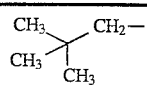 | 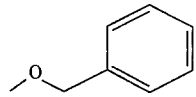 | 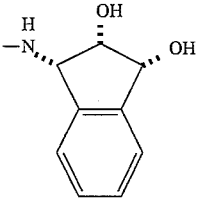 |
| 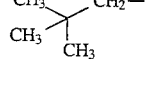 | 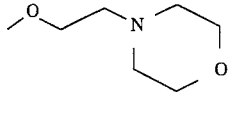 | 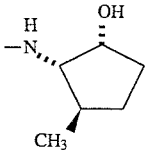 |
| 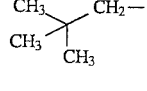 | 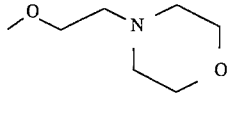 | 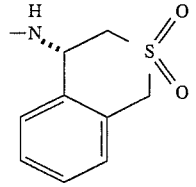 |
| 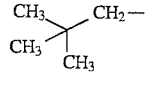 | 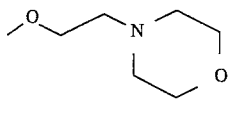 | 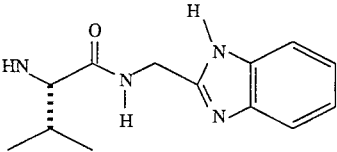 |

TABLE 4
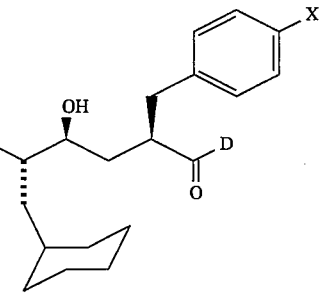
| R¹ | X | D |
|---|---|---|
| 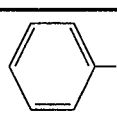 | H | 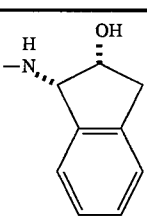 |
| 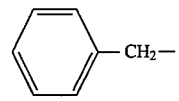 | H | 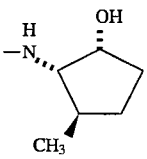 |
| 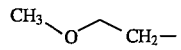 | H | 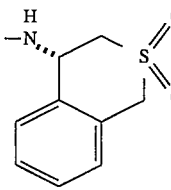 |
| 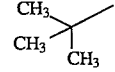 | 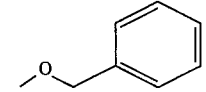 | 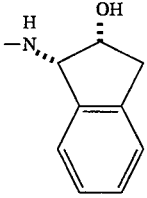 |
| 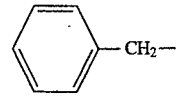 | 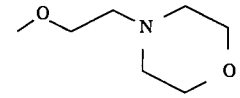 | 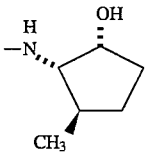 |
|  | OH | 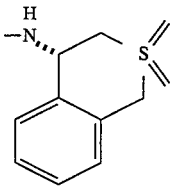 |
| 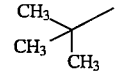 | H | 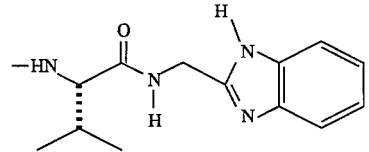 |

TABLE 4-continued
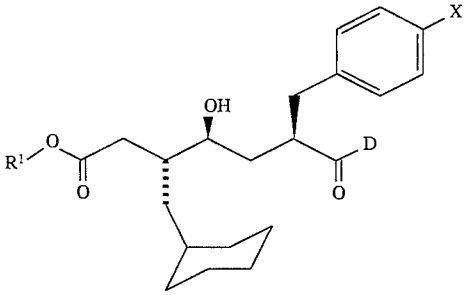
| R¹ | X | D |
|---|---|---|
|  | 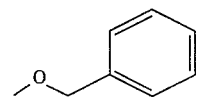 | 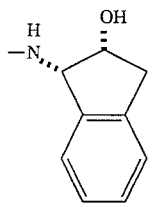 |
| 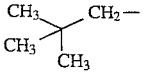 | 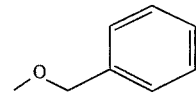 | 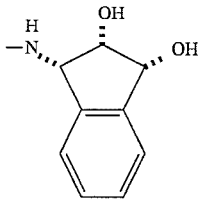 |
| 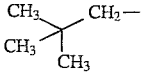 | 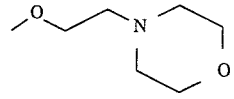 | 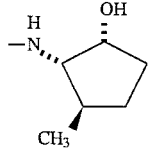 |
|  | 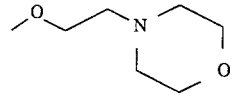 | 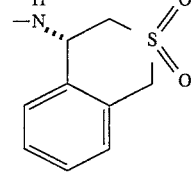 |
|  | 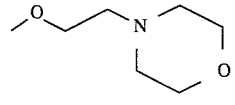 | 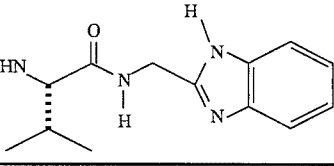 |

TABLE 5

[Structure: R¹-NH-C(=O)-CH₂-CH(CH₂-cyclohexyl)-CH(OH)-CH₂-CH(CH₂-C₆H₄-X)-C(=O)-D]

| R¹ | X | D |
|---|---|---|
| phenyl | H | (1S,2R)-1-amino-2-hydroxyindane (−NH-indanyl-OH) |
| benzyl (Ph-CH₂−) | H | (1R,2S,3R)-2-hydroxy-3-methylcyclopentylamino (−NH-cyclopentyl(OH)(CH₃)) |
| cyclopentyl | H | −NH-CH(CH₂-SO₂-CH₂-o-C₆H₄−) (cyclic sulfone) |
| tert-butyl ((CH₃)₃C−) | −O-CH₂-C₆H₅ (benzyloxy) | (1S,2R)-1-amino-2-hydroxyindane |
| benzyl (Ph-CH₂−) | −O-CH₂-CH₂-N(morpholino) | (1R,2S,3R)-2-hydroxy-3-methylcyclopentylamino |
| tert-butyl ((CH₃)₃C−) | −O-CH₂-C₆H₅ (benzyloxy) | −NH-CH(CH₂-SO₂-CH₂-o-C₆H₄−) (cyclic sulfone) |
| tert-butyl ((CH₃)₃C−) | H | −HN-CH(iPr)-C(=O)-NH-CH₂-(1H-benzimidazol-2-yl) |

TABLE 5-continued

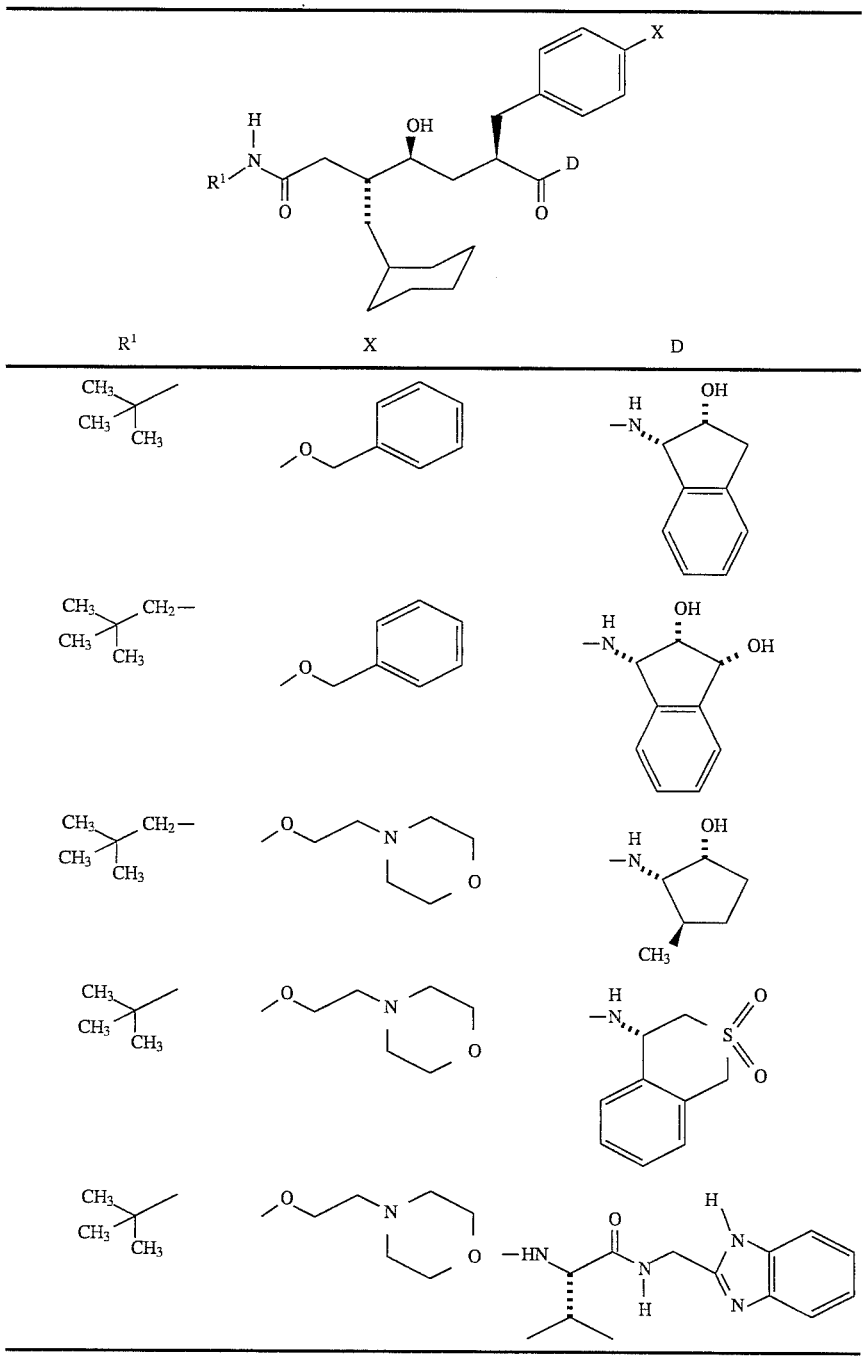

The compounds of the present invention are useful in the inhibition of HIV protease the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure of patient blood during surgery.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, ad juvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically effective amount of a compound of the present invention, or a pharmaceutically acceptable salt thereof.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetnets/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Dosage levels of the order of 0.02 to 5.0 or 10.0 grams-per-day are useful in the treatment or prevention of the above-indicated conditions, with oral doses two-to-five times higher. For example, infection by HIV is effectively treated by the administration of from 10 to 50 milligrams of the compound per kilogram of body weight from one to three times per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

It will be understood that the scope of combinations of the compounds of this invention with AIDS antivirals, immunomodulators, anti-infectives or vaccines include in principle any combination with any pharmaceutical composition useful for the treatment of AIDS.

Assay for Inhibition of Microbial Expressed Vital Protease

Inhibition studies of the reaction of the protease expressed in *Eschericia coli* with a peptide substrate [Val-Ser-Gln-Asn-(betanapthyl)Ala-Pro-Ile-Val, 0.5 mg/mL at the time the reaction is initiated] were in 50 mM Na acetate, p H 5.5, at 30° C. for 1 hour. Various concentrations of inhibitor in 1.0 ul DMSO were added to 25 ul of the peptide solution in water. The reaction is initiated by the addition of 15 ul of 0.33 nM protease (0.11 ng) in a solution of 0.133M Na acetate pH 5.5 and 0.1% bovine serum albumin. The reaction was quenched with 160 ul of 5% phosphoric acid. Products of the reaction were separated by HPLC (VYDAC wide pore 5 cm C-18 reverse phase, acetonitrile gradient, 0.1% phosphoric acid). The extent of inhibition of the reaction was determined from the peak heights of the products. HPLC of the products, independently synthesized, proved quantitation standards and confirmation of the product composition. The products of synthesis in Examples 1–6 inclusive showed $IC_{50}$ values in the range of 1–100 nM. Compounds A, B and C showed $IC_{50}$ values of between about 11.5 and about 58 nM.

EXAMPLE 1

Preparation of N-(2(R)-hydroxy-1(S)-indanyl)-5<R)-cyclohexylmethyl-9,9-dimethyl-4(S)-hydroxy-7-oxo-2(R)-phenylmethyl decaneamide (Compound B)

Step 1: Preparation of (E)-4-cyclohexyl-2-buten-1-al

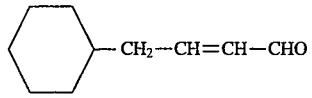

Step a: Preparation of (E)-methyl-4-cyclohexyl-2-butenoate

To a solution of 13.8 mL (158 mmol) of oxalyl chloride in 200 mL of $CH_2Cl_2$ cooled to −78° C. was added slowly 22.4 mL (315 mmol) of DMSO diluted with 25 mL of $CH_2Cl_2$. After 0.25 hr, 10 mL (71.7 mmol) of cyclohexyl ethanol was added, stirred for 0.5 hr, followed by 61.9 mL (444 mmol) of triethylamine. The mixture was allowed to slowly warm to ambient temperature and stirred 2.5 hr, followed by the addition of 35.9 g (107.5 mmol) of carbomethoxy methylene phophorane dissolved in 65 mL of $CH_2Cl_2$. After 14 hr the volatiles were removed in vacuo and the mixture was diluted with 300 mL of diethyl ether. The resultant white precipitate was removed by filtration and the organic layer was washed with aqueous 10% HCl (2×100 mL), aqueous saturated sodium bicarbonate (2×100 mL), water (3× 100 mL), brine (1×100 mL), dried over $MgSO_4$ and concentrated. The residue was purified via flash chromatography to provide a colorless oil.

Step b: Preparation of (E)-4-cyclohexyl-2-buten-1-ol

To a solution of 12.00 g (65.93 mmol) of <(E)-methyl-4-cyclohexyl-2-butenoate dissolved in 400 mL of diethyl ether cooled to −78° C. was added 215 mL (215 mmol) of DIBAL-H (1.0M in THF). After 0.5 hr the reaction was warmed to 0° C. for 0.5 hr and quenched with 300 mL of aqueous saturated solution of NaK tartrate, this stirred for 14 hr. The aqueous layer was extracted with ether (2×100 mL) and the combined organic layers were washed with water (1× 100 mL), brine (1×100 mL), dried over $MgSO_4$ and concentrated to provide (E)-4-cyclohexyl-2-buten-1-ol as colorless oil.

Step c: Preparation of (E)-4-cyclohexyl-2-buten-1-al

To 10.2 g (65.93 mmol) of (E)-4-cyclohexyl-2-buten-1-ol dissolved in 700 mL of $CH_2Cl_2$ with 10 g crushed activated 4A molecular sieves was added 11.97 g (102.2 mmol) of N-methyl morpholine-N-oxide. This mixture was cooled to 0° C. and a catalytic amount 1.197 g (3.40 mmol) of tetrapropylammonium perruthenate was added slowly. After 18 hr the mixture was filtered through celite, concentrated in vacuo, and filtered through a plug of silica gel (6× 6 cm 5% ether in hexanes) to provide the title compound as a colorless oil. Further purification by fractional distillation (bp 58°–60° C., 2 mm of Hg) afforded an oil.

Step 2: Preparation of 3-(5'-cyclohexylmethyl)-3'(S)-hydroxy-1'-oxo-2'(R)-(phenylmethyl)-4'(E)-pentenyl)-4(R)-(phenylmethyl)-2-oxazolidinone

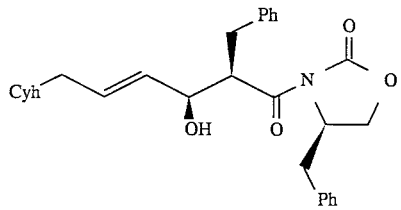

To a cold solution (0° C.) of 7.34 g (23.7 mmol) of 3-(3'-phenyl-1'-oxopropyl)-4(R)-(phenylmethyl)-2-oxazolidinone dissolved in 40 mL of CH$_2$Cl$_2$ was added 5.1 mL (28.1 mmol) of diisopropylethyl amine, followed by 25.9 mL (25.9 mmol, 1M in CH$_2$Cl$_2$) of dibutylboron trillate. The solution was stirred for 1 hr, cooled to –78° C., and 3.28 g (21.6 mmol) of freshly distilled (E)-4-cyclohexyl-2-buten-1-al dissolved in 20 mL of CH$_2$Cl$_2$ was added. The mixture stirred at –78° C. for 0.5 hr, slowly warmed to ambient temperature over 3 hr and was quenched by the addition of 10 mL p H 7.0 phosphate buffer and 30 mL of MeOH. The mixture was recooled to –78° C. and 3 mL of a 30% hydrogen peroxide solution was added and stirred for 0.5 hr. The volatiles were removed in vacuo and the aqueous layer was extracted with EtOAc exhaustively. The combined organic layers were washed with H$_2$O and brine, dried over MgSO$_4$, and concentrated. Purification of the residue by flash chromatography provided the desired product.

Step 3: Preparation of ethyl-N'-(4'(R)-phenylmethyl-2'-oxazolidinone)-carboxamido-3(R) -cyclohexylmethyl-5(R)-phenylmethyl-4(E)-heptanoate

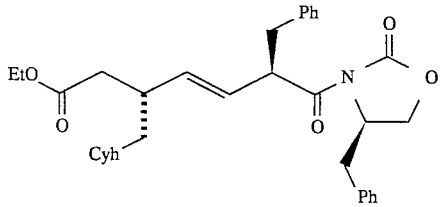

To a solution of 13.78 g (29.9 mmol) of 3-(5'-cyclohexylmethyl)-3'(S)-hydroxy-1'oxo-2'(R)-(phenylmethyl)-4'(E)-pentenyl)-4(R)-(phenylmethyl)-2-oxazolidinone in 200 mL of toluene containing a catalytic amount of isobutyric acid (0.28 mL, 3.0 mmol) was added 39.7 mL (209 mmol) of triethyl orthoacetate. This mixture was refluxed for 6 hr using a Dean Stark trap to remove 50 mL portions every hour. After 6 hr the reaction was charged with an additional 300 mL of toluene and refluxed an additional 2 hr. The mixture was diluted with 300 mL of EtOAc and the organic layer was washed with saturated NaHCO$_3$ (2×150 mL), brine (1×150 mL), dried over MgSO$_4$ and concentrated. Purification using flash chromatography provided the title product.

Step 4: Preparation of Ethyl-3(R)-cyclohexylmethyl-5(R)-phenylmethyl-4(E)-heptanedioic acid

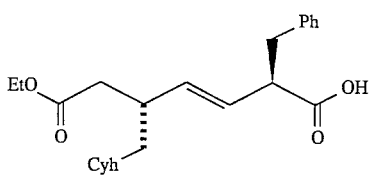

To a solution of 2.13 g (4.0 mmol) of oxazolidinone in 80 mL of THF at 0° C. was added a solution of 2.30 mL (20 mmol) of hydrogen peroxide and 0.144 g (6 mmol) of lithium hydroxide dissolved in 27 mL of water. This was stirred at 0° C. for 3 hr, slowly warming to ambient temperature. After 15 hr, the volatiles were removed in vacuo. The resulting aqueous solution was acidified with 20 mL of a 10% aqueous solution of sodium bisulfate and extracted with EtOAc (4×50 mL), the combined organic layers were washed with brine/10% NaHSO$_4$ (1:1 100 mL), dried over MgSO$_4$, and concentrated. Purification of the residue by flash chromatography afforded the title acid.

Step 5: Preparation of Ethyl-7-N'-(2(R)-hydroxy-1(S)-indanyl)-carboxamido-3(R)-cyclohexylmethyl-5(R)-phenylmethyl-4(E)-heptenoate

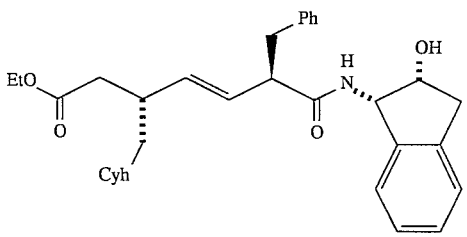

To a cold solution (0° C.) of 0.169 g (0.453 mmol) of the acid from Step 4 in 2 mL of DMF was added 0.104 g (0.544 mmol) of EDC, 0.083 g (0.544 mmol) of HOBt, 0.081 g (0.544 mmol) of 1(S)-amino-2(R)-hydroxy indane and finally 0.189 mL (1.359 mmol) of triethylamine. The mixture stirred for 18 hr slowly warming to ambient temperature, and was quenched by dilution with 100 mL of ether. The organic layer was washed with 10% aqueous sodium bisulfate (2×5 mL), saturated sodium bicarbonate (2×5 mL), water (3×5 mL), brine (1×5 mL), dried over MgSO4, and concentrated. Purification by flash column chromatography provided the title amide.

Step 6: Preparation of 7-N'-(2(R)-hydroxy-1(S)-indanyl)-carboxamido-3(R)-cyclohexylmethyl-5(R)-phenylmethyl-4(E)-heptene carboxylic acid

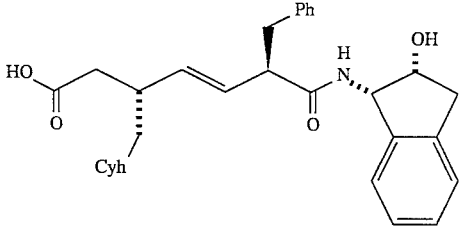

To a solution of 0.31 g (0.615 mmol) of the ethyl ester from step 5 in 6 mL of DME was added a solution of 0.147 g (6.155 mmol) of lithium hydroxide in 2 mL of water. The reaction mixture stirred for hr and the volatiles were removed in vacuo. The resulting aqueous layer was acidified to pH 3 with 10% HCl and extracted with EtOAc (4×25 mL). The combined organic layers were washed with brine (1×5 mL), dried over MgSO$_4$, and concentrated to a white solid.

Recrystallization from 10 mL of EtOAc and 10 mL of hexanes afforded the title product.

Step 7: Preparation of

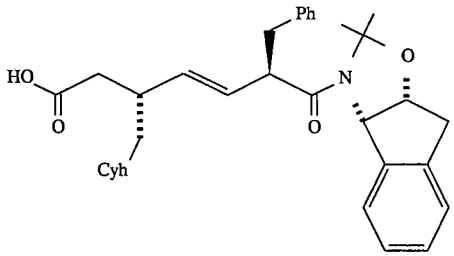

To 1.41 g (2.96 mmol) of acid suspended in 15 mL of $CH_2Cl_2$ was added a catalytic amount of pPTS (0.074 g, 0.30 mmol), followed by 0.623 mL (6.51 mmol) of 2-methoxy propene. After 5 minutes the reaction became homogeneous, and after 1 hr was quenched with 5 mL of aqueous saturated sodium bicarbonate. The aqueous layer was then extracted with $CH_2Cl_2$ (4×20 mL) and the combined organic layers were washed with brine (1×10 mL), dried over $MgSO_4$, and concentrated. This provided the title compound as a white solid.

Step 8: Preparation of

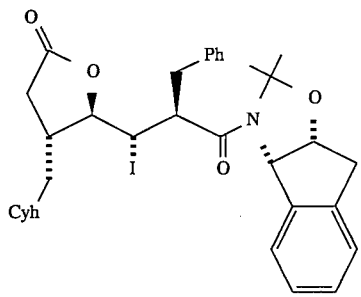

To a solution of 1.01 g (1.96 mmol) of the acid from Step 7, in 20 mL of THF was added a catalytic amount of 4,4'-thiobis(2-tert-butyl-6-methylphenol) (20 mg) and 2.20 g (9.79 mmol) of N-iodosuccinimide. The reaction was wrapped in aluminium foil and stirred for 24 hr, after which time it was charged with another 2.20 g (9.79 mmol) of N-iodosuccinimide. After an additional 6 hr the volatiles were removed in vacuo and the residue was dissolved in 100 mL of EtOAc. The organic layer was washed with saturated $Na_2S_2O_3$ (2×75 mL), saturated $NaHCO_3$ (1×75 mL), brine (1×75 mL), dried over $MgSO_4$ and concentrated. This provided the title compound as an orange foam, which was immediately subjected to hydride reduction, as described in Step 9.

Step 9: Preparation of N-(1,2-N,O-isopropylidenen-2(R)-hydroxy-1(S)-indanyl)-7-carboxylic acid lactone-5(R)-cyclohexylmethyl-4(S)-hydroxy-2(R)-phenylmethyl hexaneamide

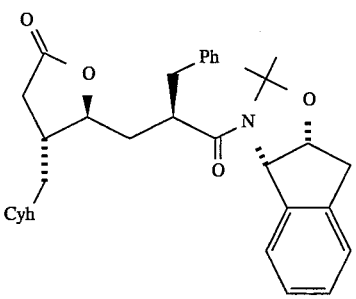

To 3.35 g (5.22 mmol) of iodide dissolved in 75 mL of toluene was added a catalytic amount of AIBN (5 mg) and 2.1 mL (7.83 mmol) of tributyltin hydride. The reaction was warmed to 60° C. and after 0.5 hr cooled to ambient temperature. The volatiles were removed in vacuo and the mixture was diluted with EtOAc (250 mL). The organic layer was washed with saturated sodium thiosulfate (1×50 mL), brine (1×50 mL), dried over $MgSO_4$ and concentrated. Purification of the residue by flash chromatography afforded the title product as a white solid.

Step 10: Preparation of

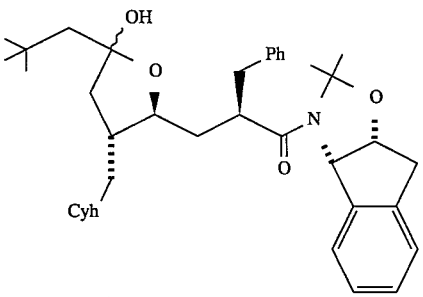

To 0.52 mL (3.90 mmol) neopentyl iodide dissolved in 10 mL of diethyl ether at −78° C. was added 4.80 mL (8.18 mmol, 1.7M in pentane) of tert-butyl lithium. This mixture was warmed to 0° C. for 0.25 hr and recooled to −78° C. for 0.5 hr, after which time a solution of 0.63 g (1.22 mmol) of the lactone from Step 9 dissolved in 10 mL of THF, precooled to −78° C., was added via cannula. The mixture stirred at −78° C. for 0.5 hr and was warmed to −20° C. for 6 hr. The reaction was then quenched with 10 mL of saturated ammonium chloride. The aqueous layer was extracted with EtOAc (4×50 mL) and the combined organic layers were washed with brine (1× 20 mL), dried over $MgSO_4$ and concentrated. Purification via flash chromatography provided a mixture of lactols as an oil.

Step 11: Preparation of N-(2(R)-hydroxy-1(S)-indanyl)-5(R)-cyclohexylmethyl-9,9dimethyl-4(S)-hydroxy-7-oxo-2(R)-phenylmethyl decaneamide

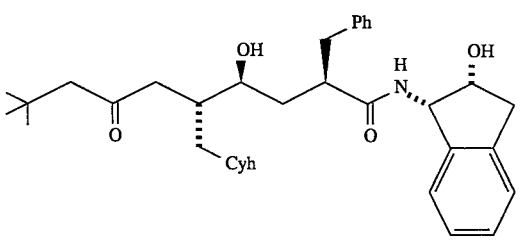

To a solution of 0.062 g (0.105 mmol) of lactols dissolved in 2 mL of acetonitrile and 1 mL of water was added 0.024 g of camphorsulfonic acid (CSA) and warmed to 70° C. After 4 hr the reaction was cooled to ambient temperature and the volatiles were removed in vacuo. The residue was dissolved in EtOAc (50 mL) and washed with aqueous saturated sodium bicarbonate (1×5 mL), brine (1×5 mL), dried over MgSO$_4$ and concentrated. The residue was purified via flash chromatography which afforded a white foam. Analysis calculated for C$_{35}$H$_{49}$NO$_4$ (0.28 CHCl$_3$): C, 72.91; H, 8.55; N, 2.41. Found: C, 72.94; H, 8.41; N, 2.61. Mass spectrum, m/e 530 (M-18).

EXAMPLE 2

Preparation of N-(2(R)-hydroxy-1(S)-indanyl)-5(R)-cyclohexylmethyl-4(S), 7-dihydroxy-2(R)-phenylmethyl heptaneamide

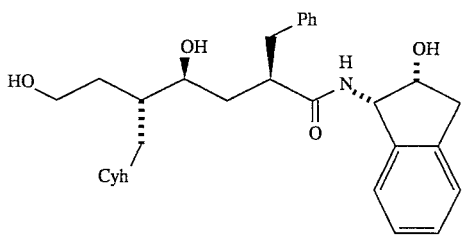

To 38 mg (0.0714 mmol) of the lactone acetonide product of Step 9, Example 1, dissolved in 1 mL of tetrahydrofuran was added 0.178 mL (0.357 mmol, 2M in THF) of a solution of lithium borohydride. The reaction mixture stirred for four hr and was quenched by the addition of 1 ml of methanol. After 0.5 hr the volatiles were removed in vacuo and the semisolid was partitioned between ethyl acetate and water. The aqueous layer was extracted with 3×25 mL of ethyl acetate and the combined organic layers were washed with brine, dried over MgSO$_4$ and concentrated. Purification by flash column chromatography provided the protected indanyl (acetonide) precursor of the title compound.

To 15 mg (0.0288 mmol) of the diol acetonide dissolved in 0.5 mL of methanol was added 5 mg (0.021 mmol) of camphorsulfonic acid. The reaction was stirred for 18 hr and neutralized with solid potassium carbonate. The solids were filtered off and the volitiles were removed in vacuo. Purification by flash column chromatography provided the title compound. Analysis calculated for C$_{30}$H$_{41}$NO$_4$ (0.46 CHCl$_3$): C, 68.44; H, 7.82; N, 2.62. Found: C, 68.39; H, 7.81; N, 2.62.

EXAMPLE 3

Preparation of N-(2(R)-hydroxy-1(S)-indanyl-6-(tertbutyloxycarbonyl)-4(S)-hydroxy-2(S)-(4-hydroxyphenyl) methyl-5(R)-phenylmethyl hexaneamide (Compound I)
Step A: Preparation of (3 RS, 5 SR, 1' SR)-3-((4-Benzyloxy) phenylmethyl)-5-(1-benzyloxymethyl-oxy-2-phenylethyl)-dihydrofuran-2-(3H)-one:

A mineral oil dispersion of sodium hydride (0.52 g) was washed twice with hexane before being suspended in 50 mL of dry tetrahydrofuran (THF). To the suspension, stirred under argon, was added a solution containing 4.0 g of 3-carboethoxy-5-((1-benzyloxymethyloxy)- 2-phenylethyl)-dihydrofuran-2(3H)-one in 70 mL of THF. After 30 minutes at room temperature the cloudy solution was immersed in a pre-heated 50° oil bath and 2.92 g of 4-benzyloxy benzyl chloride was added over 5 minutes. After stirring at 50° C. for 24 hours the mixture was cooled to room temperature, treated with 75 mL of 1.0N lithium hydroxide solution and stirring was continued for 12 hours. The THF was removed under vacuum, the residue taken up in 300 mL of water and the solution acidified with 10% citric acid. The mixture was extracted three times with ethyl ether, the combined ether extracts washed with 5% citric acid and brine. After drying over MgSO$_4$ the solvent was removed in vacuo, leaving a foam which was taken up in 350 mL of toluene. The solution was heated at reflux for 18 h, concentrated to dryness and the diastereomeric mixture was chromatographed (medium pressure liquid chromatography, or MPLC) over silica gel, eluting with 20% EtOAc in hexane to obtain the title compound: $^1$H NMR (CDC$_3$) δ1.88–2.04 (m, 1H), 2.32–2.47 (m, 1H), 2.60–3.20 (m, 5H), 4.09–4.25 (m, 2H), 4.38 (d, J=12 Hz, 1H), 4.49 (d, J=12 Hz, 1H), 4.66 (d, J=5 Hz, 1H), 4.70 (d, J=5 Hz, 1H), 4.93–5.08 (m, 2H), 6.82–7.50 (m, 19 H). Further elution afforded the diasteromer, (3 SR, 5 RS, 1 ' RS)-3-((4-benzyloxyphenylmethyl)-5-(1-benzyloxymethyloxy- 2-phenylethyl)-dihydrofuran-2(3H)-one : $^1$H NMR (CDC$_3$) δ1.95–2.25 (m, 2H), 2.60–2.96 (m, 4H), 3.16–3.28 (m, 1H), 4.10–4.80 (m, 6H), 5.00 (s, 2H), 6.90 (d, J=9 Hz, 2H), 7.10 (d, J=9 Hz, 2H), 7.16–7.48 (m, 15H).
Step B: Preparation of (3 RS, 5 SR, 1' SR)-3-(4-Benzyloxyphenylmethyl)- 5-(1-hydroxy-2-phenylethyl) dihydrofuran-2-(3H)-one To a solution containing 6.0 of (3 RS, 5 SR, 1'SR)-3-((4-benzyloxyphenylmethyl)-5-(1-benzyloxy-methyloxy-2-phenylethyl)-dihydrofuran-2-(3H)-one in 100 mL of dry dichloromethane was added 1.56 mL of thiophenol, followed by 1.79 mL of boron trifluoride etherate. After stirring for 18 hours at room temperature, the solution was chilled and diluted with 200 mL of dichloromethane, followed by 100 mL of saturated aqueous sodium bicarbonate solution. The layers were separated and the aqueous extracted once more with dichloromethane. The combined organic phases were washed with sodium bicarbonate solution, water and brine. Upon removal of the drying agent by filtration the solvent was evaporated under reduced pressure and the residue, an oil, was purified by flash chromatography (30% EtOAc in hexane) to give the title compound as an oil. $^1$H NMR (CDCl$_3$) δ1.80–3.08 (m, 9.5H), 3.67–3.80 (m, 0.5H), 3.95–4.25 (m, 2H), 5.045 (d, J=3 Hz, 1.5H), 5.095 (d, J=3 Hz, 0.5H), 6.80–7.50 (m, 14H).
Step C: Preparation of (3 RS, 5 SR)-3-(4-Benzyloxyphenylmethyl-5-(1-oxo-2-phenylethyl)-dihydrofuran-2-(3H)-one A solution containing 4.0 g of the Dess-Martin periodinane reagent in 40 mL dry dichloromethane was vigorously stirred at room temperature as a solution of the product from Step B (3.2g), dissolved in 30 mL of dichloromethane, was added. After stirring for 15 minutes at ambient temperature the reaction mixture was treated with 200 mL of ethyl ether and a solution containing 16.6 g of sodium thiosulfate in 500 mL of saturated sodium bicarbonate solution. The layers were separated, the aqueous extracted with 200 mL of ether, and the combined organic layers were washed with saturated sodium bicarbonate solution, brine, and dried (Na$_2$SO$_4$). Removal of the drying agent and solvent left an oil which was chromatographed over silica gel (30% EtOAc/hexane) to provide the pure title compound. An additional amount of this material was obtained by combining less pure fractions and subjecting them to further chromatography using a Waters Deltaprep HPLC using a m-Bondpak C-18 column eluting with a gradient of 0.1% aqueous TFA/CH3CN 0:100 to 100:0 over 35 min at 80 mL min$^{-1}$ with detection at 210 nM.: $^1$H NMR (CDCl$_3$) δ2.12–2.28 (m, 2H), 2.52–2.63 (m, 1H), 2.70–2.78 (m, 1H), 3.03 (dd, J=5, 14 Hz, 1H), 3.86 (s, 2H), 4.65 (dd, J=4, 9 Hz, 1H), 5.05 (s, 2H), 6.89 (d, J=9 Hz, 2H), 7.03 (d, J=9 Hz, 2H), 7.19–7.46 (m, 10 Hz).

Step D: Preparation of (3RS, 5SR)-5(E) (1-(1', 1'-Dimethylethoxycarbonyl) methylidene-2-phenylethyl)-3-(4-benzyloxyphenylmethyl)-dihydrofuran-2-(3H)-one A solution of 1.30 g of tert-butoxycarbonylmethylene triphenylphosphorane in 15 mL of dry benzene was added to 0.922 g of the product from Step C dissolved in 15 mL benzene and the resulting solution was stirred at room temperature for 18 hours. The solvent was removed under reduced pressure and the residue was flash chromatographed, eluting with 30% EtOAc/hexane, to provide the title compound as an oil: $^1$H NMR (CDCl$_3$) δ1.49 (s, 9H), 1.95–2.14 (m, 2H), 2.65–2.86 (m, 2H), 3.02–3.09 (m, 1H), 3.48 (d, J=14.5 Hz, 1H), 4.47 (d, J=14.5 Hz, 1H), 4.58 (t, J=5 Hz, 1H), 5.05 (s, 2H), 5.97 (s, 1H), 6.90 (d, J=9 Hz, 2H), 7.03 (d, J=9 Hz, 2H), 7.15–7.47 (m, 10H).

Step E: Preparation of (2-RS, 4-SR)-7-tert-Butyl-1-hydrogen-2-(4-benzyloxyphenylmethyl)-4-(1', 1'-dimethylethyl-1,1-dimethylsilyloxy)-5-phenylmethyl-5(E)-heptene dioate The product of Step D, 0.441 g, was dissolved in 4 mL of 1,2-dimethoxyethane and to the solution were added 1.0 mL of 1.0N lithium hydroxide and 2 mL of water. After stirring at room temperature for 4 h the mixture was concentrated on a rotary evaporator, the residue was suspended in acetonitrile and the mixture concentrated to dryness. This procedure to remove water azeotropically with acetonitrile was repeated twice more and the residual white solid was then pumped dry at 0.1 mm Hg overnight. The solid was dissolved in 6 mL of dry DMF and 0.600 g of imidazole and 0.655 g of tert.-butyl dimethylsilyl chloride were added. After stirring for 24 h at room temperature, 6.0 mL of methanol was added and the solution was stirred for 3 h before concentrating the mixture to dryness under vacuum. The residue was partitioned between EtOAc and 5% citric acid. The aqueous phase was extracted twice more with ETOAc, the combined ETOAc layers washed with 5% citric acid, water and brine. After drying over magnesium sulfate the drying agent and solvent were removed to afford the crude product as an oil. Chromatography over silica gel (25% ETOAc in hexane) provided the pure title compound as an oil which was used directly in Step F.

Step F: Preparation of tert-Butyl 7-N-(1(S)-Indanyl-2(R)-hydroxy)-carboxamido-6(R)-(4- benzyloxyphenylmethyl)-4(S)-hydroxy-3-phenylmethyl-2(E)-heptenoate A solution containing the product of Step E (0.418 g), 1-hydroxybenztriazole hydrate (0.130 g) and dimethyl-3-(3-dimethylaminopropyl) carbodiimide hydrochloride (0.152 g), in 5 mL of dry DMF was treated with N-methylmorpholine (0.085 mL) until the pH of the solution was 8.5. After stirring for 18 h the solution was concentrated to dryness under reduced pressure and the residue was partitioned between 25 mL of EtOAC and 70 mL of water. The layers were separated and the aqueous phase was adjusted to pH 6.0 by addition of 10% citric acid. Following extraction with ETOAc (2×25 mL) the combined acidic ETOAc extracts were washed (5% citric acid, water, saturated sodium bicarbonate, brine) and dried (Na$_2$SO$_4$). This solution was concentrated to an oil which was purified by flash chromatography (25% ETOAc in hexane): a single diastereomer, tert-butyl 7-N-(1(S)-indanyl-2(R)-hydroxy)-carboxamido-6(S)-(4-benzyloxyphenylmethyl)-4(R)-(1', 1'-dimethylethyl-1,1-dimethylsilyloxy)-3-phenylmethyl-2(E)-heptenoate eluted first. Continued elution provided the desired diastereomer, tert-butyl 7-N-(1(S)-indanyl-2(R)-hydroxy)-carboxamido-6(R)-(4-benzyloxyphenylmethyl)-4(S)-(1', 1'-dimethylethyl-1,1-dimethylsilyloxy)- 3-phenylmethyl- 2(E)-heptenoate, as an oil. This product was dissolved in 2 mL of dry THF and was treated with 2.0 mL of a 1.0N solution of tetrabutylammonium fluoride in THF. After stirring for 18 hours the solvent was removed in vacuo and the residue was taken up in 50 mL of ETOAc. After washing with water and brine, the solution was dried (Na$_2$SO$_4$) and concentrated to an oily solid. An analytical sample of the title compound was prepared by trituration with ethyl ether: m.p. 126°–128° C.

Step G:. N-(2(R)-hydroxy-1(S)-indanyl-6-(tertbutyloxycarbonyl-4(S)-hydroxy-2(S)-(4-hydroxyphenyl)-methyl-5(R)-phenylmethyl hexaneamide.

The olefinic product of Step F was dissolved in 50 mL of 95% ethanol and 80 mg of palladium hydroxide on carbon (Pearlman's catalyst) was added. The mixture was stirred under an atmosphere of hydrogen (balloon) for 18 hours. Following removal of the catalyst by filtration through Supercel the solvent was removed under reduced pressure and the solid which remained was purified by chromatography over silica gel, eluting with 35% to 50% EtOAc in hexane: m.p. 141°–144° C. (a mixture of diastereomers at C-3).

EXAMPLE 4

Preparation of N-(2(R)-hydroxy-1(S)-indanyl)-N'-cyclopentyl-2(R)-(4-hydroxyphenyl)methyl-4(S)-hydroxy-5(R)-phenylmethyl heptane-1,7-dicarboxamide (Compound J)

Step A: Preparation of (3RS, 5SR)-5-(E) (1-(Cyclopentylcarbamoyl) methylidene-2-phenylethyl)-3-(4-benzyloxyphenylmethyl)-dihydrofuran-2-(3H)-One The product from Example 3, Step D, 0.560 g, was dissolved in 10 mL of dry dichloromethane and the solution was treated with 2 mL of trifluoroacetic acid. After stirring at ambient temperature for 18 h the solvents were removed under reduced pressure and the foam residue was pumped dry at 0.1 mm Hg. The resulting intermediate carboxylic acid was dissolved in 15 mL of dry acetonitrile and the solution was stirred at 0° C. as 0.495 g of benzotriazol-1-yloxytris(dimethylamino)phosphonium hexafluorophosphate, 0.135 mL of cyclopentylamine, and 0.115 mL of triethylamine were added. The cooling bath was removed and the reaction was allowed to proceed at room temperature for 24 hours. Saturated aqueous sodium chloride (30 mL) was added and the aqueous mixture was extracted twice with ETOAc. The combined organic phases were washed with 5% aqueous HCl saturated sodium bicarbonate solution, and brine, then dried over Na$_2$SO$_4$. Removal of the drying agent and solvent left an oil which was purified by flash chromatography (40% ETOAc in hexane) to afford the title compound: $^1$H NMR (CDCl$_3$) δ1.50–2.15 (m, 10H), 2.62–2.88 (m, 2H), 2.98 (d, J=4 Hz, 1H), 3.03 (d, J=4 Hz, 1H), 3.42 (d, J=14 Hz, 1H), 4.20–4.32 (m, 1H), 4.55 (t, J=6 Hz, 1H), 4.73 (d, J=14 Hz, 1H), 5.03 (s, 2H), 5.91 (s, 1H), 6.08 (broad d, J=9 Hz, 1H), 6.88 (d, J=8 Hz, 2H), 7.02 (d, J=8.5 Hz, 2H), 7.10–7.50 (m, 10 Hz).

Step B: 7-Cyclopentylamino-1-hydrogen 2-(RS)-(4-benzyloxyphenylmethyl-4-(SR) (1',1'-dimethylethyl-1,1-dimethylsilyloxy)-5-phenylmethyl-5(E)-heptene dioate The product from Step A, 0.450 g, dissolved in 5 mL of 1,2-dimethoxy ethane, was treated with 1.0 mL each of 1.0N. lithium hydroxide and water. After 3 h at room temperature, the mixture was concentrated to dryness under vacuum and the residue was suspended in 5 mL of 10% citric acid and extracted with 3×25 mL of ethyl ether. The combined ether extracts were washed (brine), dried (MgSO4) and concentrated to dryness. The residue was dissolved in 6 mL of dry DMF and to the solution were added 0.665 g of tert-butyl dimethylsilyl chloride and 0.601 g of imidazole.

After stirring for 18 h at room temperature the reaction mixture was treated with 5 mL of abs methanol and stirring was continued for 3 hours before the mixture was concentrated to dryness in vacuo. The residue was suspended in 50 mL of water, acidified to pH 3 with 10% citric acid and extracted three times with ethyl ether. The combined ether extracts were washed with water, brine and dried (MgSO$_4$) and the solvent removed. Purification of the oil which remained by medium pressure chromatography, elution with 15 to 40% ETOAc in CHCl$_3$, afforded the title compound.

Step C: N-(2(R)-Hydroxy-1(S)-indanyl)-N'-cyclopentyl-2(RS)-(4-benzyloxyphenylmethyl)-4-(SR)-(1',1'-dimethyl-ethyl-1,1-dimethylsiiyloxy)-5-phenylmethyl-5(E)-heptene-1,7-dicarboxamide A solution containing the product of Step B (0.286 g), 1-hydroxybenztriazole hydrate (0.066 g), 1(S)-amino-2(R)-hydroxyindane (0.093 g), and dimethyl-3-(3-dimethylaminopropyl)carbodiimide hydrochloride (0.094 g) in 5 mL of dry DMF was treated with N-methylmorpholine to pH 8.5. After stirring for 18 h the solution was concentrated under vacuum and the residue was partitioned between 50 mL each of ETOAc and water. The layers were separated, the aqueous extracted twice with ETOAc and the combined organic layers were washed with 5% citric acid, saturated aqueous sodium bicarbonate, brine, and dried (Na$_2$SO$_4$). Following removal of the solvent there remained a yellow oil which was subjected to medium pressure chromatography, elution with ETOAc/hexane (30/70). In this manner the diastereomeric products were separated, providing N-(2R)-hydroxy-1(S)-indanyl)-N'-cyclopentyl-2(SR)-(4-b enzyloxyphenylmethyl)-4-(RS)-(1',1'-dimethylethyl-1,1-dimethylsilyloxy)-5-phenylmethyl-5(E)-heptene-1,7-dicarboxamide: $^1$H NMR (CDCl$_3$) δ–0.10–3.26 (m, 32H), 4.10–4.30 (m, 2H), 4.54–4.67 (m, 1H), 4.69 (d, J=14 Hz, 1H), 5.06 (s, 2H), 5.21–5.29 (m, 1H), 5.76 (d, J=8 Hz, 1H), 5.90 (d, J=8 Hz, 1H), 6.08 (s, 1H), 6.57 (d, J=7.5 Hz, 1H), 6.93 (d, J=8 Hz, 2H), 7.10 (d, J=8 Hz, 2H), 7.13–7.50 (m, 13 H). Continued elution of the column provided the title compound which was carried on to the next step without further purification. $^1$H NMR (CDCl$_3$) δ0.80–3.07 (m, 26 H), 3.22 (d, J=13.5 Hz, 1H), 4.05–4.17 (m, 2H), 4.19–4.32 (m, 1H), 4.82 (d, J=13.5 Hz, 1H), 5.04 (s, 2H), 5.30 (dd, J=5, 7.5 Hz, 1H), 5.41 (d, J=7.5 Hz, 1H), 5.61 (d, J=9 Hz, 1H), 6.01 (s, 1H), 6.90 (d, J=8.5 Hz, 2H), 7.04–7.46 (m, 16H).

Step D N-(2(R)-hydroxy-1(S)-indanyl)-N'-cyclopentyl-2(R)-4-hydroxyphenyl)methyl-4(S)-hydroxy-5(R),phenylmethyl heptane-1,7-dicarboxamide A solution containing 0.125 g of N-(2(R)-hydroxy-1(S)-indanyl)-N'-cyclopentyl-2(RS)-(4-benzyloxyphenylmethyl)-4-(SR)-(1',1'-dimethylethyl-1,1-dimethylsilyloxy)-5-phenylmethyl-5(E)-heptene-1,7-dicarboxamide from Step C in 1.0 mL of freshly distilled THF was treated with 1.5 mL of 1.0N tetrabutylammonium fluoride in THF. After 24 h stirring at room temperature, the solution was concentrated to dryness in vacuo and the residue was stirred in 5 mL of 5% citric acid for 2 h. The mixture was filtered and the solid which was collected was purified by silica gel chromatography, eluting with CHCl$_3$-ETOAc (1:1), affording 0.080 g of pure N-(2(R)-hydroxy-1(S)-indanyl)-N'-cyclopentyl-2(R)-(4-benzyloxyphenylmethyl)-4(S)-hydroxy-5(E)-phenylmethylheptene-1,7-dicarboxamide. This material was dissolved in 30 mL of 95% ethanol, 25 mg of palladium hydroxide (Pearlman's catalyst) was added, and the mixture was stirred under a hydrogen atmosphere (balloon) for 20 hours. The catalyst was removed by filtration through Supercel/glass fiber paper and the material which remained following evaporation of the solvent was chromatographed on silica gel, eluting with a mixture of CHCl$_3$, CH$_3$OH, NH$_4$OH (98:2:0.2) to provide N-(2(R)-hydroxy-1(S)-indanyl)-N'-cyclopropyl-2(R)-(4-hydroxyphenylmethyl)-4(S)-hydroxy-5(S) phenylmethyl-heptane-1,7-dicarboxamide as an oil. Trituration with ethyl ether afford ed a white solid, m.p. 193°–196° C. dec. Continued elution of the column with CHCl$_3$, CH$_3$OH, NH$_4$OH (95:5:0.5) provided 10 mg of the title compound as a white solid, m.p. 194°–197° C. dec.

EXAMPLE

Preparation of N-(2(R)-hydroxy-1(S)-indanyl)-5(R)-cyclohexylemthyl-4(S)-hydroxy-7-oxo-2(R)-phenylmethyl undecaneamide (Compound A)

Step 1: Preparation of N-(1,2-N,O-isopropylidenen-2(R)-hydroxy-1(S)-indanyl)-7-oxo lactol-5(R)cyclohexylmethyl-4(S)-hydroxy-2(R)-phenylmethyl undecaneamide

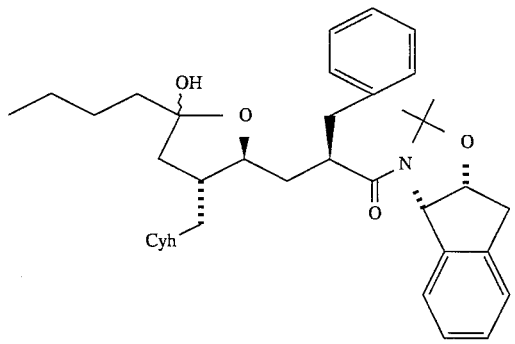

To 97 mg of N-(1,2-N,O-isopropylidenen-2(R)-hydroxy-1(S)-indanyl)-7-carboxylic acid lactone-5(R)-cyclohexylmethyl-4(S)-hydroxy-2(R)-phenyimethyl hexaneamide (0.19 mmol) prepared in Example 1, step 9, dissolved in 2 mL of THF and cooled to –78° C. was added 0.18 mL of n-BuLi (0.28 mmol). After 1 hour the reaction was warmed to 0° C. and after 1 hour at 0° C. the reaction was quenched with 5 mL of saturated NH$_4$Cl. The aqueous layer was extracted with ETOAc (3× 25 mL) and the combined organic layers were washed with saturated NaHCO$_3$ (1×10 mL), brine (1×10 mL), dried over MgSO$_4$ and concentrated. Purification via flash chromatography afforded a mixture of lactols as an oil. Mass spectrum, m/e 573 (2,M$^+$), 556 (100, M-17), 498 (20), 321(11).

Step 2: Preparation of N-(2(R)-hydroxy-1(S)-indanyl)-5(R)-cyclohexylmethyl-4(S)-hydroxy-7-oxo-2(R)-phenylmethyl undecaneamide The acetonide product of step 1 above was hydrolyzed as in step 11 of Example 1, to provide the title product. Analysis calculated for C$_{34}$H$_{47}$NO$_4$ (0.30 ETOAc): C, 76.51; H,8.88; N, 2.62. Found: C, 75.47; H, 8.75; N, 2.84. Mass spectrum, m/e 533 (1,M$^+$), 516 (100, M-17), 498 (20), 321(11).

EXAMPLE 6

Preparation of N-(2(R)-hydroxy-1(S)-indanyl)-5(R)-cyclohexylmethyl-4(S)-hydroxy-7-oxo-2(R)-phenylmethyl-8-(2'-tetrahydrofuran), octaneamide (Compound C)

The title compound was obtained employing substantially the same procedure as described in Example 1, except that the neopentyl iodide used in Step 10 was replaced with tetrahydrofuran methyl iodide. Analysis calculated for C$_{34}$H$_{47}$NO$_4$ (0.32 CHCl$_3$): C, 70.71; H, 7.95; N, 2.33. Found: C, 70.79; H, 7.86: N, 2.66. Mass spectrum, m/e 561 (1,M$^+$), 544 (100, M-17).

EXAMPLE 7

Preparation of N-(2(R)-hydroxy-1(S)-indanyl)-5(R)-cyclohexylmethyl-9,9-dimethyl-4(S)-hydroxy-2(R)-((4-benzyloxyphenyl) methyl)-7-oxo decaneamide (Compound E)

The title compound is obtained employing substantially the same procedure as described in Example 1, except replacing the 3-(3-phenyl-1'-oxopropyl)-4(R)-(phenylmethyl)-2-oxazotidinone used in Step 2 with 3-(3'-phenyl-1-oxopropyl)-4(R)-(4-benzyloxyphenylmethyl)-2-oxazolidinone.

EXAMPLE 8

Preparation of N-(2(R)-hydroxy-1(S)-indanyl)-5(R)-cyclohexylmethyl-9,9-dimethyl-4(S)-hydroxy-2(R)-((4-(2-(4-morpholinyl)ethoxy)phenyl)methyl)-7-oxo decaneamide (Compound D)

Step 1: Preparation of N-(2(R)-hydroxy-1(S)-indanyl)-5(R)-cyclohexylmethyl-9,9-dimethyl-4(S)-hydroxy-2(R)-((4-hydroxyphenyl)methyl)-7-oxo decaneamide Employing catalytic hydrogenation, the product of Example 6 is dissolved in ethanol, 10 mole percent Pd on carbon catalyst is added and the reaction is maintained under an atmosphere of hydrogen. The reaction can be monitored by TLC (thin layer chromatography) until complete, the catalyst removed by filtration, and the solvent removed in vacuo to obtain the title compound.

Step 2: Preparation of N-(2(R)-hydroxy-1(S)-indanyl-5(R)-cyclohexylmethyl-9,9-dimethyl-4(S)-hydroxy-2(R)-((4-(2-(4-morpholinyl)-ethoxy) phenyl)methyl)-7,-oxo decaneamide The product of Step 1 above is alkylated with 4-(2-chloroethyl)morphine hydrochloride in dioxane and cesium carbonate. The reaction mixture is concentrated and purified via flash column chromatography to provide the title product.

EXAMPLE 9

Preparation of N-(4(S)-3,4-dihydro-1H-2,2-dioxobenzothiopyranyl)-5(R)-cyclohexylmethyl-9,9-dimethyl-4(S)-hydroxy-7-oxo-2(R)-phenylmethyl decaneamide (Compound F)

Employing substantially the same procedure as in Example 1, but omitting step 7 and step 11 therein, and substituting 4(S)-amino-3,4-dihydro- 1H-2,2-dioxobenzothiopyran for the 1(S)-amino-2(R)-hydroxyindane used in Step 5 therein, the title compound is obtained.

EXAMPLE 10

Preparation of N-(2(R)-hydroxy-1(S)-indanyl)-5(R)-cyclohexylmethyl-9,9-dimethyl-4(S),7-dihydroxy-2(R)-phenylmethyl decaneamide (Compound G)

By treating the product of Example 1 with $NaBH_4$ in methanol at 0° C. and quenching the reaction with water followed by extractive workup, the title compound is obtained.

EXAMPLE 11

Preparation of N-(2(R)-hydroxy-1(S)-indanyl)-5(R)-cyclohexylmethyl-9,9-dimethyl-4(S)-hydroxy-7-oxime-2(R)-phenylmethyl decaneamide (Compound H)

By treating the product of Example 1 with hydroxyl amine hydrochloride in pyridine, followed by concentration and aqueous work up, the title compound is obtained.

EXAMPLE 12

Preparation of 3-carboethoxy-5-((1-benzyloxymethoxy)-2-phenylethyl)-dihydrofuran-2(3H)-one Step A: Preparation of 3-benzyloxymethoxy-4-phenyl-1-butene Diisopropylethylamine (18 mL, 0.103 mol) was added to a solution containing 13.34 g of 1-phenyl- 3-buten-2-ol (*J. Org. Chem.* 39, 578 (1974)) and 15.0 mL (0.108 mol) of benzylchloromethyl ether in 200 mL of anhyd. $CH_2Cl_2$ under an atmosphere of argon. The mixture was stirred overnight at room temperature, after which time the solvent was removed on a rotary evaporator and the residue was partitioned between ethyl ether and 0.1N HCl. The layers were separated and the aqueous phase was extracted twice with ethyl ether. The combined ether extracts were washed successively with 10% citric acid, water and brine before drying over sodium sulfate. Evaporation of the solvent in vacuo left crude title compound as an oil which was used directly in the next step. $^1$H NMR ($CDCl_3$) δ2.88–2.91 (m, 2H), 4.23 (s, 2H), 4.36 (q, J=7 Hz, 1H), 4.62–4.88 (m, 4H), 5.21–5.29 (m, 2H), 5.72–5.85 (m, 1H), 7.18–7.40, (10H).

Step B: Preparation of 4-phenyl-3-(benzyloxymethoxy)-1, 2-epoxybutane

Dry m-chloroperbenzoic acid was prepared by suspending 100 g of 50% mCPBA (meta-chloroperoxybenzoic acid) in 1 L of $CH_2Cl_2$. A small amount of insoluble material was removed by filtration and the clear filtrate was transferred to a 2 L separatory funnel. After 1 hour the water which had separated was removed and the organic phase was dried over magnesium sulfate. The mixture was filtered into a clean flask containing 22.3 g (0.083 mol) of 3-benzyloxymethoxy-4-phenyl-1-butene and 49.25 g (0.409 mol) of magnesium sulfate in 200 mL of $CH_2Cl_2$, cooled in an ice bath. The reaction mixture was allowed to warm to room temperature and stirring was continued until TLC (25% ETOAc in hexane) indicated the reaction was complete (6 days). The white solid was filtered off and the filtrate was washed with water, twice with saturated aqueous sodium bicarbonate, then exhaustively with aqueous sodium bisulfite until a KI/starch paper test for peroxides was negative. The $CH_2Cl_2$ phase was concentrated to an oil on a rotary evaporator and the oil was taken up in 500 mL of ethyl ether. After washes with 300 mL volumes of dilute aqueous sodium bisulfite (1x), dilute aqueous sodium bicarbonate (3x), and brine, the ether layer was dried (sodium sulfate) and concentrated to give 24 g of an oil which contained the title compound as a diastereomeric mixture of erythro and threo epoxides. Purification and partial separation of the diastereomers were achieved through chromatography on silica gel, eluting with 15% ETOAc in hexane: the first isomer to elute was assigned the erythro configuration: $^1$H NMR ($CDCl_3$) δ2.76–3.06 (m, 5H), 3.70–3.79 (m, 1H), 4.18 (d, $J_A$=12 Hz, 1$H_A$), 4.29 (d, $J_B$=12 Hz, 1$H_B$), 4.54 (d, $J_A$=7 Hz, 1$H_A$), 4.76 (d, $J_B$=7 Hz, 1$H_B$), 7.15–7.36 (m, 10H). Continued elution produced a mixture of stereoisomers, followed by elution of pure threo isomer: $^1$H NMR ($CDCl_3$) δ2.36 (m, 1H), 2.68 (t, J=4 Hz, 1H), 2.83–3.06 (m, 3H), 3.59 (d, $J_A$=7 Hz, 1$H_A$), 3.64 (d, $J_B$=7 Hz, 1$H_B$), 4.32 (d, $J_A$=12 Hz, 1$H_A$), 4.40 (d, $J_B$=12 Hz, 1$H_B$), 4.70 (d, $J_A$=7Hz, 1$H_A$), 4.93 (d, $J_B$=7 Hz, 1$H_B$), 7.21–7.36 (m, 10H).

Step C: Preparation of 3-carboethoxy-5-((1-benzyloxymethoxy)-2-phenylethyl)-dihydrofuran-2(3H)-one:

To a solution of freshly prepared sodium ethoxide (2.98 g, 0.115 g atom of sodium in 130 mL of abs. ethanol) was added 21 mL (0.137 mol) of diethylmalonate. After 30 min at room temperature, under argon, the solution was treated with 11.14 g (0.039 mol) of a mixture of epoxides, the products of Step B, dissolved in 75 mL of ethanol. Stirring was continued for 24 hours and then the reaction mixture was poured onto 1000 g of crushed ice. The mixture was acidified to pH 3 by addition of 10% citric acid and extracted three times with ethyl ether. The combined ether layers were washed successively with 5% citric acid and brine and then were dried over sodium sulfate. Column chromatography (silica gel, eluting with 25% ETOAc in hexane) was employed to remove excess malonate and effect purification of the title compound: $^1$H NMR (CDCl$_3$) δ1.20–1.35 (m, 3H), 2.25–3.08 (m, 4H), 3.43–4.84 (m, 9H), 7.14–7.40 (m, 10H). This material was used without further purification in Step A of Example 3.

Where noted in the above examples, positive fast atom bombardment (FAB) mass spectroscopy was used to determine the listed mass spectrum data. While the foregoing specification teaches the principles of the present invention, with examples provided for the purpose of illustration, it will be understood that the practice of the invention emcompasses all of the usual variations, adaptations, or modifications, as come within the scope of the following claims and its equivalents.

What is claimed is:

1. A compound of the formula

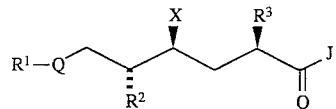

wherein

X is —OH,

Q is

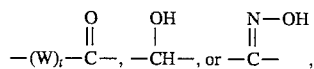

wherein

W is —O— or —NH—, and t is zero or 1;

R$^1$ is —C$_{1-6}$ alkyl unsubstituted or substituted with tetrahydro-furyl or —C$_{5-7}$ cycloalkyl;

R$^2$ is —CH$_2$—C$_{5-10}$ cycloalkyl or —CH$_2$-phenyl,

R$^3$ is —CH$_2$-phenyl, unsubstituted or substituted with one or more of
1) hydroxy,
2) C$_{1-3}$ alkoxy unsubstituted or substituted with one or more of
   i) —OH,
   ii) C$_{1-3}$ alkoxy, or
   iii) phenyl,
3) —O(CH$_2$)$_2$-morpholinyl, or
4) —O—((CH$_2$)$_m$O)$_p$—R wherein m is 2–5, p is 1–4 and R is hydrogen or C$_{1-4}$ alkyl;

and J is

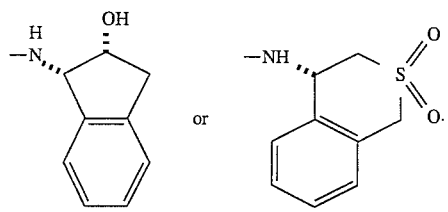

2. A compound selected from the group consisting of:
(a) N-(2(R)-hydroxy-1(S)-indanyl)-5(R)-cyclohexylmethyl-4(S)-hydroxy-7-oxo-2(R)-phenylmethyl undecaneamide,
(b) N-(2(R)-hydroxy-1(S)-indanyl)-5(R)-cyclohexylmethyl-9,9-dimethyl-4(S)-hydroxy-7-oxo-2(R)-phenylmethyl decaneamide,
(c) N-(2(R)-hydroxy-1(S)-indanyl)-5(R)-cyclohexylmethyl-4(S)-hydroxy-7-oxo-2(R)-phenylmethyl-8-(2'-tetrahydrofuran) octaneamide,
(d) N-(2(R)-hydroxy-1(S)-indanyl)-5(R)-cyclohexylmethyl-9,9-dimethyl-4(S)-hydroxy-2(R)-((4-(2-(4-morpholinyl) ethoxy)phenyl)methyl)-7-oxo decaneamide
(e) N-(2(R)-hydroxy-1(S)-indanyl)-5(R)-cyclohexylmethyl-9,9-dimethyl-4(S)-hydroxy-2(R)-((4-benzyloxyphenyl) methyl)-7-oxo decaneamide,
(f) N-(4(S)-3,4-dihydro-1H-2,2-dioxobenzothiopyranyl)-5(R)-cyclohexylmethyl-9,9-dimethyl-4(S)-hydroxy-7-oxo-2(R)-phenylmethyl decaneamide,
(g) N-(2(R)-hydroxy-1(S)-indanyl)-5(R)-cyclohexylmethyl-9,9-dimethyl-4(S),7-dihydroxy-2(R)-phenylmethyl decaneamide,
(h) N-(2(R)-hydroxy-1(S)-indanyl)-5(R)-cyclohexylmethyl-9,9-dimethyl-4(S)-hydroxy-7-oxime-2(R)-phenylmethyl decaneamide,
(i) N-(2(R)-hydroxy-1(S)-indanyl)-6-(tertbutyloxycarbonyl)-4(S)-hydroxy-2(S)-(4-hydroxyphenyl)methyl-5(R)-phenylmethyl hexaneamide, or
(j) N-(2(R)-hydroxy-1(S)-indanyl)-N'-cyclopentyl-2(R)-(4-hydroxyphenyl)methyl-4(S)-hydroxy-5(R)-phenylmethyl heptane-1,7-dicarboxamide, or a pharmaceutically acceptable salt thereof.

3. A pharmaceutical composition comprising a compound of claims 1 or 2 and a pharmaceutically acceptable carrier.

4. The pharmaceutical composition of claim 3 for use in the treatment of AIDS, in the treatment by infection of HIV, or in the inhibition of HIV protease.

5. A method of treating AIDS, comprising administering to a mammal in need of such treatment an effective amount of a compound of claims 1 or 2.

6. A method of treating infection by HIV, comprising administering to a mammal in need of such treatment an effective amount of a compound of claims 1 or 2.

7. A method of inhibiting HIV protease, comprising administering to a mammal in need of such treatment an effective amount of a compound of claims 1 or 2.

* * * * *